United States Patent
Griffin et al.

(10) Patent No.: US 7,901,511 B2
(45) Date of Patent: Mar. 8, 2011

(54) METHOD OF PROCESSING LIGNOCELLULOSIC FEEDSTOCK FOR ENHANCED XYLOSE AND ETHANOL PRODUCTION

(75) Inventors: Robert Griffin, Ottawa (CA); Colin Nicholson, Ottawa (CA); Corinne Mott, Kanata (CA); Jeffrey S. Tolan, Ottawa (CA); Vijay Anand, Brossard (CA)

(73) Assignee: Iogen Energy Corporation, Ontario (CA)

( * ) Notice: Subject to any disclaimer, the term of this patent is extended or adjusted under 35 U.S.C. 154(b) by 926 days.

(21) Appl. No.: 10/467,741

(22) PCT Filed: Feb. 27, 2002

(86) PCT No.: PCT/CA02/00244

§ 371 (c)(1), (2), (4) Date: Jan. 12, 2004

(87) PCT Pub. No.: WO02/070753

PCT Pub. Date: Sep. 12, 2002

(65) Prior Publication Data

US 2004/0231661 A1 Nov. 25, 2004

Related U.S. Application Data

(60) Provisional application No. 60/272,353, filed on Feb. 28, 2001.

(51) Int. Cl.
- C13K 1/02 (2006.01)
- C13D 1/14 (2006.01)
- C12P 7/06 (2006.01)
- C12P 7/08 (2006.01)
- C12P 7/10 (2006.01)

(52) U.S. Cl. .................. 127/37; 435/161; 435/163; 435/165; 127/44

(58) Field of Classification Search ........................ None
See application file for complete search history.

(56) References Cited

U.S. PATENT DOCUMENTS

| | | | |
|---|---|---|---|
| 2,284,500 A * | 5/1942 | Warth | 127/37 |
| 3,627,636 A * | 12/1971 | Jaffe et al. | 435/158 |
| 4,137,395 A * | 1/1979 | Buckl et al. | 536/124 |
| 4,160,695 A | 7/1979 | Dietrichs et al. | |
| 4,168,988 A | 9/1979 | Riehm et al. | |
| 4,181,796 A | 1/1980 | Dietrichs et al. | |
| 4,237,226 A | 12/1980 | Grethlein | |
| 4,326,892 A | 4/1982 | Madsen et al. | |
| 4,427,584 A * | 1/1984 | LeGrand et al. | 530/500 |
| 4,461,648 A | 7/1984 | Foody | |
| 4,556,430 A | 12/1985 | Converse et al. | |
| 4,857,145 A | 8/1989 | Villavicencio | |
| 5,198,074 A | 3/1993 | Villavicencio et al. | |
| 5,536,325 A | 7/1996 | Brink | |
| 5,628,830 A | 5/1997 | Brink | |
| 5,705,369 A * | 1/1998 | Torget et al. | 435/105 |
| 5,846,787 A | 12/1998 | Ladisch et al. | |
| 6,090,595 A | 7/2000 | Foody et al. | |
| 6,251,643 B1 | 6/2001 | Hansen et al. | |
| 6,333,181 B1 | 12/2001 | Ingram et al. | |
| 2003/0041982 A1 | 3/2003 | Prior | |

FOREIGN PATENT DOCUMENTS

| | | |
|---|---|---|
| IL | 34444 A * | 6/1973 |
| JP | 47-055856 | 6/1972 |
| WO | WO 95/13362 | 5/1995 |
| WO | WO 97/42307 | 11/1997 |

OTHER PUBLICATIONS

Tseaa Shambe, John F Kennedy "Acid hydrolysis of chaotropically pretreated millet stalk, acha and rice straws and conversion of the products of ethanol" Enzyme Microbo Technol. vol. 7, 1985 p. 115.*
Tom Richard "Substrate Compostition Table" Cornell Waste Management Institute Dec. 24, 1996.*
Answers.com, "Leach" definition, http://www.answers.com/leaching?cat=technology&print=true, accessed Mar. 25, 2008 3:35:58 PM.*
Tom Richard "Substrate Composition Table:Cornell Composting Science and Engineering" 9 pgs 1996 accessed at http://compost.css.cornell.edu/calc/lignin.noframes.html (9 of 9)Dec. 17, 2008.*
J. J. Rackis "Soybean Protein : Uses, Problems, and Potential" J. Am. Oil Chemists' Soc., Apr. 1977 (vol. 54) p. 290.*
Sigma-Aldrich; "Particle Size Conversion Table" 2pgs This information is also provided on p. T848 of the Aldrich 2003-2004 Catalog/Handbook of Fine Chemicals.*

(Continued)

*Primary Examiner* — Irene Marx
*Assistant Examiner* — Thane Underdahl
(74) *Attorney, Agent, or Firm* — Fitzpatrick, Cella, Harper & Scinto

(57) ABSTRACT

The present invention provides a method of producing xylose from lignocellulosic feedstock. The method comprises disrupting lignocellulosic feedstock; leaching the lignocellulosic feedstock by contacting the feedstock with at least one aqueous solution for a period greater than about 2 minutes to produce a leached feedstock and a leachate; removing the leachate from the leached feedstock; acidifying the leached feedstock to a pH between about 0.5 and about 3 to produce an acidified feedstock, and; reacting the acidified feedstock under conditions which disrupt fiber structure and hydrolyze a portion of hemicellulose and cellulose of the acidified feedstock, to produce a composition comprising xylose and a pretreated feedstock. The xylose may be purified from the pretreated feedstock or it may be converted to ethanol with the pretreated feedstock.

53 Claims, 10 Drawing Sheets

OTHER PUBLICATIONS

J. Fernindez-Bolanos et al. "Characterization of the lignin obtained by alkaline delignification and of the cellulose residue from steam-exploded olive stones" Bioresource Technology 68 (1999) 121-132.*

Nazik N. Boulos et al. "Water holding capacity of selected soluble and insoluble dietary fibre" International Journal of Food Properties, vol. 3, Issue 2 Jul. 2000, pp. 217-231.*

Grethlein, Hans E., "Chemical Breakdown of Cellulosic Materials," *J. Appl. Chem. Biotechnol.*, 1978, 28, pp. 296-308.

Jenkins, B.M., et al., "Measurements of the Fouling and Slagging Characteristics of Banagrass (*Pennisetum purpureum*) Following Aqueous Extraction of Inorganic Constituents," *Making a Business from Biomass*, pp. 705-718.

King, C. Judson, *Separation Processes*, 2d. Ed., McGraw-Hill, 1980, pp. 2-9.

Keim, C.R., Chapter 1, "Wet Milling of Grain for Alcohol Production," *The Alcohol Textbook*, Nottingham University Press, 1995, pp. 1-9.

Tolan, J.S., Chapter 9, "Alcohol production from cellulosic biomass: the logen process, a model system in operation," *The Alcohol Textbook*, 3d. Ed., Nottingham University Press, 1999, pp. 117-127.

Foody, Patrick, et al., "Optimization of Steam Explosion Pretreatment," Final Report Submitted to U.S. Dept. of Energy, Contract No. DE-AC02-79ETZ3050, Iotech Corporation, Apr. 1980.

International Search Report, dated Feb. 10, 2003, for corresponding International Application No. PCT/CA02/00244.

International Preliminary Examination Report, dated Jul. 2, 2003, for corresponding International Application No. PCT/CA02/00244.

Richard, "Substrate Composition Table", Cornell Composting Science and Engineering (1996) 1-9.

Rackis, "Soybean Protein: Uses, Problems and Potential", J. Am. Oil Chemists' Soc., vol. 54 (1977) 290-94.

Grohmann, et al., "The Role of Ester Groups in Resistance of Plant Cell Wall Polysaccharides to Enzymatic Hydrolysis", Applied Biochemistry and Biotechnology, vol. 20/21 (1989) 45-61.

* cited by examiner

METHOD OF PROCESSING LIGNOCELLULOSIC FEEDSTOCK FOR ENHANCED XYLOSE AND ETHANOL PRODUCTION

This application is the U.S. national phase application of PCT International application No. PCT/CA02/00244, which claims the benefit of U.S. provisional application No. 60/272,353, filed on Feb. 28, 2001.

The present invention relates to pretreatment processes for the conversion of lignocellulosic feedstocks into sugars. More specifically, the present invention relates to pretreatment processes for the conversion of lignocellulosic feedstocks into sugars and the subsequent conversion of sugars to ethanol.

BACKGROUND OF THE INVENTION

The possibility of producing ethanol from cellulose-containing lignocellulosic feedstocks such as wood, cultivated crops like switch grass and waste agricultural fibers such as wheat straw and oat hulls has received much attention due to the availability of large amounts of feedstocks, the desirability to avoid burning or landfilling cellulosic waste materials, and the cleanliness of ethanol as a fuel compared to gasoline.

The efficient conversion of cellulose from lignocellulosic material into glucose and the subsequent fermentation of glucose to ethanol represents a major challenge. Cellulose, which is the primary constituent of lignocellulosic fibers, consists of a crystalline structure that is very resistant to breakdown, as is hemicellulose, the second most prevalent component. The conversion of lignocellulosic fibers to ethanol requires: 1) liberating cellulose and hemicellulose from lignin or increasing the accessibility of cellulose and hemicellulose within the lignocellulosic feedstock to cellulase enzymes, 2) depolymerizing hemicellulose and cellulose carbohydrate polymers to free sugars and, 3) fermenting the mixed hexose and pentose sugars to ethanol.

Methods used to convert cellulose to glucose typically include acid hydrolysis (reviewed by Grethlein; *Chemical Breakdown Of Cellulosic Materials*, J.APPL.CHEM. BIOTECHNOL. 28:296-308 (1978)). Acid hydrolysis involves the use of either concentrated or dilute acids. The concentrated acid process uses 72% by weight sulfuric acid or 42% by weight hydrochloric acid at room temperature to dissolve the cellulose, followed by dilution to 1% acid and heating to 100° C. to 120° C. for up to three hours to convert cellulose oligomers to glucose monomers. This process produces a high yield of glucose, but the recovery of the acid, and the specialized construction materials required for the apparatus to carry out this process are serious disadvantages. Similar problems are encountered when concentrated organic solvents are used for cellulose conversion.

U.S. Pat. No. 5,536,325 describes a two-step process for the acid hydrolysis of lignocellulosic material to glucose. The first (mild) step depolymerizes the hemicellulose to xylose and other sugars. The second step depolymerizes the cellulose to glucose. Even though the process uses low levels of acid, the amount of acid required for the hydrolysis of the feedstock is substantial, and the resulting yield of glucose from cellulose is poor.

Other methods for converting lignocellulosic material to ethanol use a multistep procedure in which the lignocellulosic material is first pretreated at high temperature and pressure and often in the presence of various chemicals. This pretreatment process is thought to increase the accessibility of cellulose within the lignocellulosic fibers for subsequent conversion steps. As a large portion of the cellulose within untreated lignocellulosic material is unaccessible for subsequent enzymatic conversion steps, the efficiency of this pretreatment phase can profoundly influence the overall efficiency and commercial application of the entire conversion process.

Among the more successful pretreatment processes for the conversion of lignocellulosic feedstock into glucose, are dilute acid prehydrolysis processes. One effective dilute acid hydrolysis pretreatment is steam explosion as disclosed in U.S. Pat. No. 4,461,648 (Foody process, which is herein incorporated by reference). In the Foody process, biomass is loaded into a vessel known as a steam gun. Up to 1% acid is optionally added to the biomass in the steam gun or in a presoak. The steam gun is then filled very quickly with steam and held at high pressure for a set length of time, known as the cooking time. Once the cooking time elapses, the vessel is depressurized rapidly to expel the pretreated biomass. As a result of the rapid depressurization, the Foody process has been termed "steam explosion". Specific parameters for steam explosion pretreatments are set out in U.S. Pat. No. 4,461,648; and Foody, et al, Final Report, *Optimization of Steam Explosion Pretreatment*, U.S. DEPARTMENT OF ENERGY REPORT ET230501 (Apr. 1980), which are herein incorporated by reference.

U.S. Pat. No. 4,237,226 describes the dilute-acid pretreatment of oak, newsprint, poplar, and corn stover by a continuous plug-flow reactor, a device that is similar to an extruder. Rotating screws convey a feedstock slurry through a small orifice, where mechanical and chemical action break down the fibers to increase the accessibility to cellulose.

One shortcoming of dilute acid prehydrolysis is the high acid requirement. For a clean feedstock, such as washed hardwood, the sulfuric acid demand is 0.5% to 1% of the dry weight of the feedstock. For agricultural fibers, which can contain high levels of silica, salts, and alkali potassium compounds from the soil, the acid demand is about 10-fold higher, reaching 5% to 7% by weight of feedstock. This adds significant additional cost to the process. A second drawback of using large amounts of acids in a prehydrolysis process is that an acidified feedstock must be neutralized to a pH between about 4.5 and about 5 prior to enzymatic hydrolysis with cellulase enzyme. The amount of caustic soda used to neutralize acidified feedstock is proportional to the amount of acid used to acidify the feedstock. Thus, high acid usage results in high caustic soda usage, which further increases the cost of processing lignocellulosic feedstock to ethanol.

Another drawback of steam explosion and other dilute acid pretreatment processes is that the while the treatment conditions significantly increase accessibility to cellulose, these same conditions result in the destruction and loss of xylose. Xylose is not as stable as the other sugars and has a tendency to break down in acid pretreatment conditions. The breakdown of xylose decreases the overall sugar yield that can be obtained from lignocellulosic feedstocks and this in turn decreases ethanol yield.

U.S. Pat. No. 5,198,074 and U.S. Pat. No. 4,857,145 (which are herein incorporated by reference) disclose washing chiped feedstock with water prior to removing a soluble fraction, used for the production of ethanol, and a fibre fraction for use in pulp and paper production. There is no disclosure of the use of the pretreated fraction for the production of xylose or ethanol.

U.S. Pat. No. 5,846,787 discloses processes for pretreating cellulosic materials prior to enzymatic conversion with cellulases. The process involves heating the cellulosic materials in water at a temperature at or above their glass transition temperature while maintaining the pH of the reaction medium in a range that avoids autohydrolysis of the cellulosic materials. The method is performed in place of a dilute acid or steam explosion pretreatment process. The water used in the pretreatment process of U.S. Pat. No. 5,846,787 is heated under pressure to a temperature in excess of 100° C., and thus requires a significant amount of energy to heat the water to such temperatures and is expensive and inefficient.

U.S. Pat. No. 4,326,892 discloses a method of improving the recovery of sugar from sugar beets. Sugar beets contain primarily sucrose, with little cellulose. The method comprises washing sugar beets to remove impurities therefrom, removing the outer layer of the of the washed sugar beets, slicing the sugar beets and extracting the slice sugar beets with an aqueous solution. After this washing, the relative amount of cellulose in the resulting beet pulp is increased. There is no suggestion that the pulp obtained by this process may be used for the production of xylose or ethanol as described herein.

U.S. Pat. No. 6,251,643 discloses a method for processing biomass using a screw press. In this method, following separation of a liquid phase from the solid phase, the solid phase is heated under pressure, to a temperature of 100-170° C., to produce a vapour treated phase of solids which is then further processed. The use of high temperatures to produce the vapour treated phase results in the denaturing of any protein component within the solid phase. Furthermore, the process described in this document results in a relatively low yield of ethanol from biomass (180-250 liters ethanol per metric ton dry material).

The publication entitled Wet Milling of Grain for Alcohol Production by Lyons et al., in Chapter 1 of The Alcohol Textbook 1995 (Nottingham University Press) discloses wet milling of corn in alcohol production. The corn kernel comprises approximately 70% starch and contains little cellulose. After starch removal, the resulting corn fiber is high in cellulose. The reference teaches soaking clean corn in tanks for about 20 to 40 hours with steep water/acid containing about 1600 ppm $SO_2$, at a temperature of about 52° C. This steeping is the first step in removing starch from corn. However, the reference does not teach the use of the corn fiber for the production of xylose or ethanol as described herein.

The publication entitled "Separation Processes" by C. Judson King (1980, McGraw-Hill Book Company) discloses processing of sugar cane. Sugar cane is primarily sugar, with little cellulose. The reference teaches washing sugar cane with jets of water to remove field debris, followed by chopping the sugar cane into short sections, passing the sections through high pressure rollers and adding water to remove the available sugar. The sugar solution is processed and refined into raw sugar, black molasses and other products. After sugar removal, the remaining cane pulp (bagasse) is high in cellulose content. There is no suggestion that the remaining bagasse maybe used for xylose or ethanol production as outline herein.

Jenkins et al., (Measurements of the Fouling and Slagging Characteristics of Banagrass (*Pennisetum purpureum*) Following Aqueous Extraction of Inorganic Constituents. In: Making a Business from Biomass in Energy, Environment, Chemicals, Fibers and Materials. Proceedings of the 3$^{rd}$ Biomass Conference of the Americas, Montreal, Quebec, Canada, August 24-29. Pergamon (Elsevier Science)) discloses the washing of biomass fuel by aqueous extraction to control slagging and fouling in combustion systems burning banagrass. There is no suggestion that the washed lignocellulosic biomass maybe used for xylose or ethanol production as described herein.

Methods that improve xylose yield during acid hydrolysis improve the cost efficiency of converting lignocellulosic feedstock to sugars. Furthermore, methods that reduce the amount of acid required for dilute acid pretreatments increase the cost efficiency of ethanol production.

There is a need in the art to reduce the amount of acid which must be used in a pretreatment process. Further, there is a need in the art to increase xylose yield from lignocellulosic feedstocks subjected to pretreatment processes.

It is an object of the present invention to overcome disadvantages of the prior art.

The above object is met by a combination of the features of the main claims. The sub claims disclose further advantageous embodiments of the invention.

SUMMARY OF THE INVENTION

The invention relates to pretreatment processes for the conversion of lignocellulosic feedstocks into sugars. More specifically, the present invention relates to pretreatment processes for the conversion of lignocellulosic feedstocks into sugars and the subsequent conversion of sugars to ethanol.

According to an embodiment of the present invention there is provided a method of producing xylose from lignocellulosic feedstock comprising greater than about 20% (w/w) cellulose. The method comprises a) leaching the lignocellulosic feedstock by contacting the feedstock with at least one aqueous solution for a period greater than about 2 minutes to produce a leached feedstock and a leachate;

b) removing the leachate from the leached feedstock; and c) reacting the acidified feedstock under conditions which disrupt fiber structure and hydrolyze a portion of hemicellulose and cellulose of the acidified feedstock, to produce a composition comprising xylose and a pretreated feedstock.

The present invention relates to the above method, wherein following the step of removing (step b)), is a step of acidifying the leached feedstock to a pH between about 0.5 and about 3 to produce an acidified feedstock.

The lignocellulosic feedstock may be selected from one or more of the following C4 grasses: switch grass, cord grass, rye grass, miscanthus, and a combination thereof, or sugar cane bagasse, soybean stover, corn stover, rice straw, rice hulls, barley straw, corn cobs, wheat straw, oat hulls, corn fiber, wood fiber, or a combination thereof. Preferably the lignocellulosic feedstock comprises an AX/NSP ratio of about 0.35 to about 0.45, such as wheat straw, wheat chaff, switch grass, corn stover, corn cobs, oat hulls, or a combination thereof. The lignocellulosic feedstock may also comprise newsprint, cardboard, sawdust and combinations thereof. More preferably the lignocellulosic feedstock comprises oat hulls, wheat straw, switch grass, or a combination thereof.

Also according to the method of the present invention as defined above, the composition comprising xylose may comprise xylose polymer, xylose monomer or a combination thereof. The composition may comprise other components such as salts, sugars and the like.

Further, according to the method of the present invention as defined above, the lignocellulosic feedstock preferably comprises mechanically disrupted feedstock. Preferably, the lignocellulosic feedstock is mechanically disrupted to pass through 20 mesh, more preferably 40 mesh. Mechanical disruption maybe performed by shredding, milling, chopping, chipping, grinding or a combination thereof. Preferably, mechanical disruption is performed by Hammer milling, Wiley milling, Szego milling or a combination thereof.

Also according to the method of the present invention as defined above, leaching is performed for a period between about 2 minutes and about 2 hours, and at a temperature between about 5° C. and about 95° C. Preferably the leaching is performed at a temperature between about 20° C. and about 80° C., and more preferably between about 60° C. and about 80° C. Furthermore, the aqueous solution employed in leaching lignocellulosic feedstock comprises about 0.25 to about 10 times the maximum water holding capacity per kilogram of dry lignocellulosic feedstock. Leaching may also comprise a plurality of leaching stages. In embodiments of the method of the present invention wherein leaching comprises multiple Teachings, preferably leaching comprises about 2 to about 4 leaching stages. Further, the leaching stages may be performed in a countercurrent fashion.

Also according to the method of the present invention as defined above, the aqueous solution may comprise plant water, process water, fresh water or a combination thereof. Preferably the aqueous solution comprises a solution of pH about 3 to about 9, and contains less than about 10 g/l of dissolved impurities. The pH may be adjusted using NaOH, $H_2SO_4$ or a combination thereof.

Further, according to the method of the present invention as defined above, leaching preferably removes between about 50% to about 100%, preferably 70% to 100% of the total leachable buffering agents from the lignocellulosic feedstock. The leachate may be sampled during leaching, following leaching or both, and the leaching parameters, such as leaching time, or the number of leaching stages in a multi-stage leaching may be adjusted accordingly.

According to the present invention there is provided a composition produced by the method of the present invention as defined above, wherein the composition comprises xylose and a pretreated feedstock. Preferably, the lignocellulosic feedstock yields xylose in the range of about 150 mg to about 260 mg of xylose per gram of feedstock. The pretreated feedstock has increased accessibility to being digested during a treatment with cellulase enzyme. Further, the composition produced by the method of the present invention, the pretreated feedstock or both may be treated with cellulase enzyme to convert cellulose to glucose, and this treatment may be followed by fermenting glucose to products such as, but not limited to ethanol, or lactic acid. Glucose may also be chemically hydrogenated to sorbitol or converted to other products such as acetic acid, citric acid, ascorbic acid, propanediol, butanediol, acetone, butanol, or a combination thereof.

Also according to the method of present invention as defined above, the lignocellulosic feedstock preferably comprises cellulose in an amount greater than about 20%, more preferably greater than about 30%, still more preferably greater than about 40% (w/w). The lignocellulosic feedstock may also comprise lignin in an amount greater than about 5%, more preferably in an amount greater than about 10% (w/w). The lignocellulosic feedstock may also comprise a combined amount of sucrose, fructose and starch in an amount less than about 20%, preferably less than about 10% (w/w). The weight percentages disclosed above are relative to the mass of the lignocellulosic feedstock as it exists in its natural state, prior to any processing.

The present invention also provides a method of producing xylose from lignocellulosic feedstock comprising,
 a) leaching a mechanically disrupted lignocellulosic feedstock, the leaching comprising contacting the feedstock with at least one aqueous solution for a period of about 2 minutes to about 2 hours at a temperature of about 20° C. to about 80° C. using a volume of aqueous solution which is between about 0.25 and about 10 times the maximum water holding capacity of the disrupted lignocellulosic feedstock, to produce a leached feedstock and a leachate;
 b) removing the leachate from the leached feedstock;
 c) acidifying the leached feedstock to a pH between about 0.5 and about 3 to produce an acidified feedstock, and;
 d) reacting the acidified feedstock under conditions which disrupt fiber structure and hydrolyze a portion of hemicellulose and cellulose of the acidified feedstock, to produce a composition comprising xylose and a pretreated feedstock.

Also according to the present invention, there is provided a method of producing ethanol from a lignocellulosic feedstock comprising greater than about 20% (w/w) cellulose, the method comprising,
 a) leaching the lignocellulosic feedstock by contacting the feedstock with at least one aqueous solution for a period greater than about 2 minutes to produce a leached feedstock and a leachate;
 b) removing the leachate from the leached feedstock;
 c) acidifying the leached feedstock to a pH between about 0.5 and about 3 to produce an acidified feedstock, and;
 d) reacting the acidified feedstock under conditions which disrupt fiber structure and hydrolyze a portion of hemicellulose and cellulose of the acidified feedstock, to produce a composition comprising xylose and a pretreated feedstock;
 e) treating the composition comprising xylose and pretreated feedstock with cellulase under conditions which hydrolyse cellulose in the pretreated feedstock to glucose, producing a sugar solution comprising xylose and glucose, and;
 f) fermenting the sugar solution to ethanol.

Also according to the present invention, there is provided a method of producing ethanol from a lignocellulosic feedstock comprising greater than about 20% (w/w) cellulose, the method comprising,
 a) leaching the lignocellulosic feedstock by contacting the feedstock with at least one aqueous solution for a period greater than about 2 minutes to produce a leached feedstock and a leachate;
 b) removing the leachate from the leached feedstock;
 c) acidifying the leached feedstock to a pH between about 0.5 and about 3 to produce an acidified feedstock, and;
 d) reacting the acidified feedstock under conditions which disrupt fiber structure and hydrolyze a portion of hemicellulose and cellulose of the acidified feedstock, to produce a composition comprising xylose and a pretreated feedstock, and;
 e) treating the composition with a microrganism under conditions which permit fermentation of the xylose in the composition to ethanol.

Also according to the present invention, there is provided a method of producing ethanol from a lignocellulosic feedstock comprising greater than about 20% (w/w) cellulose, the method comprising,
 a) leaching the lignocellulosic feedstock by contacting the feedstock with at least one aqueous solution for a period greater than about 2 minutes to produce a leached feedstock and a leachate;
 b) removing the leachate from the leached feedstock;
 c) acidifying the leached feedstock to a pH between about 0.5 and about 3 to produce an acidified feedstock, and;
 d) reacting the acidified feedstock under conditions which disrupt fiber structure and hydrolyze a portion of hemicellulose and cellulose of the acidified feedstock, to produce a composition comprising xylose and a pretreated feedstock;

e) separating the pretreated feedstock from the composition;

f) treating the pretreated feedstock with cellulase under conditions which hydrolyse cellulose in said pretreated feedstock to glucose, producing a sugar solution comprising glucose, and;

g) fermenting the sugar solution to ethanol.

Thus, it is contemplated that xylose produced in the pretreatment of lignocellulosic feedstock may be fermented in combination with glucose, or separate from glucose produced by cellulose hydrolysis of the pretreated feedstock.

The present invention also provides a method for preparing a lignocellulosic feedstock comprising:

a) preconditioning the lignocellulosic feedstock to produce a preconditioned feedstock;

b) incubating the preconditioned feedstock within a leaching bath to produce a leached feedstock; and c) crushing the leached feedstock to produce a pressate and a solid feedstock.

In the method as described above, the step of preconditioning (step a)) may comprise heating the lignocellulosic feedstock by steam to about 80° C. for about 1 minute, and in the step of incubating (step b)), debris may be removed from the leaching bath. Furthermore, in the step of incubating (step b)), the preconditioned feedstock may be incubated from about 5 to about 30 minutes, and wherein in the step of crushing (step c)), the pressate comprises soluble protein which is further processed for animal feed.

The present invention also pertains to a lignocellulosic feedstock processing system comprising, a feedstock handling device; a preconditioner capable of receiving the feedstock from the handling device, the preconditioner in communication with a steam source, the steam source for heating the feedstock, a first transfer device, for conveying the feedstock within, and from, the preconditioner to a leaching bath, a second transfer device for mixing the feedstock within the leaching bath and conveying the feedstock from the leaching bath to a press, a third transfer device for conveying pressed feedstock from the press to a second leach stage, and multi-press, to produce processed lignocellulosic feedstock.

Using the methods as described herein for the processing of biomass, high yields of ethanol can be obtained from about 300-340 liter ethanol per metric ton biomass. Another advantage of the method as described herein, over prior art methods for the preparation of lignocellulosic feedstock for xylose, ethanol, or both xylose and ethanol production, is that protein is recovered from the feedstock prior to any steam and acid treatments. These steam and acid treatments denature protein within the feedstock, and hydrolyse labile amino acids, for example but not limited to lysine, that are important for high quality animal feeds. As the protein is recovered from the feedstock processed according to the present invention prior to denaturing process, the protein is of a high quality, and can be used for animal feed.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 6 shows several aspects of the present invention.

FIG. 8 shows the release of xylose from a lignocellulosic feedstock in the presence of increasing acid concentration during pretreatment.

DESCRIPTION OF PREFERRED EMBODIMENT

Figure 1:
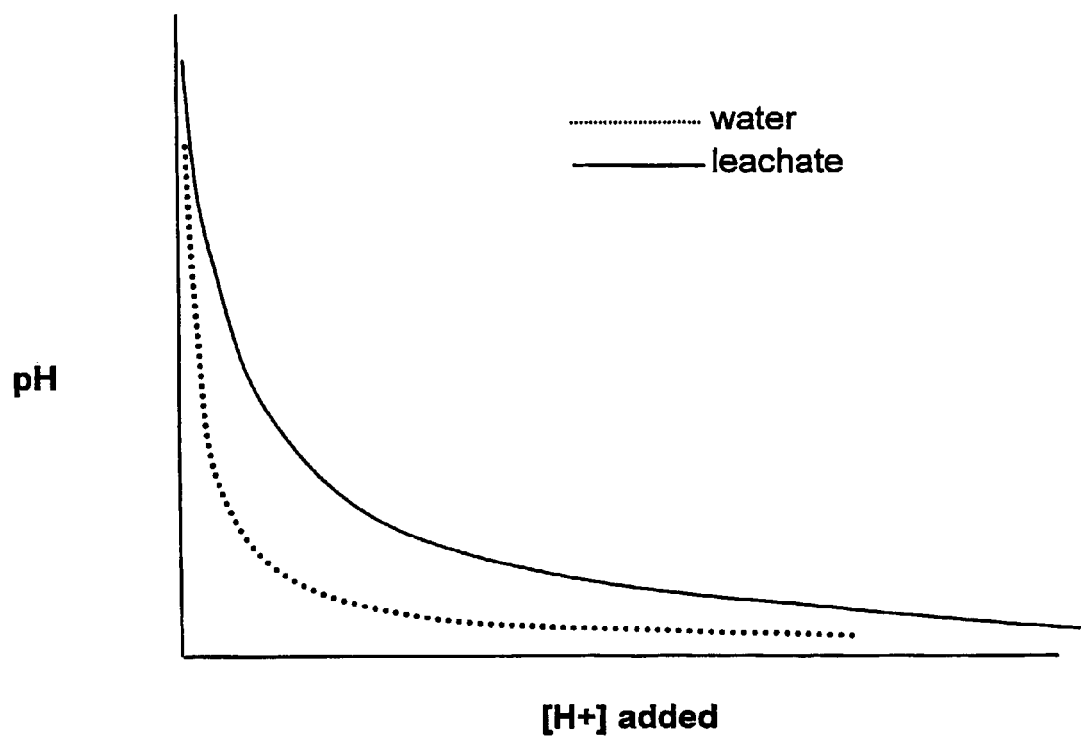
FIG. 1 shows a graphical representation showing the amount of acid required to titrate water (dashed line) versus a leachate (solid line).

The invention relates to pretreatment processes for the conversion of lignocellulosic feedstocks into sugars. More specifically, the present invention relates to pretreatment processes for the conversion of lignocellulosic feedstocks into sugars and the subsequent conversion of sugars to ethanol.

The following description is of a preferred embodiment by way of example only and without limitation to the combination of features necessary for carrying the invention into effect.

According to an embodiment of the present invention there is provided a method of producing xylose from lignocellulosic feedstock comprising:

a) leaching the lignocellulosic feedstock by contacting the feedstock with at least one aqueous solution for a period greater than about 2 minutes to produce a leached feedstock and a leachate;
b) removing the leachate from the leached feedstock; and
c) pretreating the leached feedstock to produce a composition comprising xylose, pretreated feedstock, or both xylose and pretreated feedstock.

The composition comprising xylose and pretreated feedstock, or each of xylose or the pretreated feedstock may be used for further processing to produce product of interest, for example but not limited to, ethanol, as described herein.

A non-limiting example of a method to pretreat the lignocellulosic feedstock, as identified in step c), above, is:

i) acidifying the leached feedstock to a pH between about 0.5 and about 3 to produce an acidified feedstock, and;
ii) reacting the acidified feedstock under conditions which disrupt fiber structure and hydrolyze a portion of hemicellulose and cellulose of the acidified feedstock, to produce a composition comprising xylose and a pretreated feedstock.

However, any method within the art may be used as required for the preparation of a pretreated feedstock. Other examples include, but are not limited to, the methods disclosed in U.S. Pat. Nos. 6,333,181; 5,198,074; 4,857,145; 4,556,430; 4,461,648; 4,237,226; 5,536,325; 5,846,787 (which are incorporated herein by reference).

By the term "lignocellulosic feedstock" it is meant any type of plant biomass such as but not limited to non-woody plant biomass, cultivated crops such as, but not limited to grasses, for example but not limited to C4 grasses, such as switch grass, cord grass, rye grass, miscanthus, or a combination thereof, or sugar cane bagasse, soybean stover, corn stover, rice straw, rice hulls, barley straw, corn cobs, wheat straw, oat hulls, corn fiber, recycled wood pulp fiber, sawdust, hardwood, softwood or a combination thereof. Further, the lignocellulosic feedstock may comprise cellulosic waste material such as, but not limited to newsprint, cardboard, sawdust and the like. Lignocellulosic feedstock may comprise one species of fiber or alternatively, lignocellulosic feedstock may comprise a mixture of fibers that originate from different lignocellulosic feedstocks. Further, the lignocellulosic feedstock may comprise fresh lignocellulosic feedstock, partially dried feedstock, fully dried feedstock or a combination thereof. Preferably, the lignocellulosic feedstock comprises fully dried feedstock.

Preferably, the lignocellulosic feedstock comprises cellulose in an amount greater than about 20%, more preferably greater than about 30%, still more preferably greater than about 40% (w/w). The lignocellulosic feedstock may also comprise lignin in an amount greater than about 5%, more preferably in an amount greater than about 10% (w/w). The lignocellulosic feedstock may also comprise a combined amount of sucrose, fructose and starch in an amount less than about 20%, preferably less than about 10% (w/w). The weight percentages disclosed above are relative to the mass of the lignocellulosic feedstock as it exists in its natural state, prior to any processing.

It is preferred that the lignocellulosic feedstock comprise a mechanically disrupted feedstock. Mechanical disruption of lignocellulosic feedstock may be performed according to any method known in the art provided that the method is capable of reducing the lignocellulosic feedstock into particles of an adequate size. For example, but not to be considered limiting, mechanical disruption of straw preferably results in pieces of straw having a length less than about 0.5 inches and an average diameter less than about 2 mm. Preferably, mechanical disruption of lignocellulosic feedstock produces particles which pass through about 20 mesh, preferably 40 mesh. Without wishing to be limiting, mechanical disruption of lignocellulosic feedstock may be performed by chopping, chipping, grinding, milling, shredding or the like. Preferably, mechanical disruption is performed by milling, for example, but not limited to, Szego milling, Hammer milling or Wiley milling. However, the method of the present invention also contemplates the use of undisrupted lignocellulosic feedstock comprising a particle size which may pass through about 20 mesh, preferably about 40 mesh.

It is preferred that mechanical disruption of lignocellulosic feedstock is performed on feedstock that is substantially dry, that is, the lignocellulosic feedstock comprises less than about 40% moisture, preferably between about 0% and about 40% moisture. More preferably from about 0% to about 10% moisture. However, the method of the present invention contemplates mechanical disruption of wet lignocellulosic feedstock or concurrent mechanical disruption and leaching of lignocellulosic feedstock. Furthermore, wet or moist lignocellulosic feedstock may also be dried prior effecting mechanical disruption of the feedstock.

In a preferred embodiment the lignocellulosic feedstock comprises a feedstock with a high AX/NSP ratio. AX/NSP is the ratio of arabinan plus xylan to non-starch polysaccharides and can be measured for any feedstock based on the analytical procedures described in U.S. Pat. No. 6,090,595 which is herein incorporated by reference. AX/NSP is calculated from EQUATION (1):

$$AX/NSP=(xylan+arabinan)/(xylan+arabinan+cellulose) \quad (1)$$

wherein the xylan, arabinan, and cellulose contents of the feedstocks is measured according to the procedures in EXAMPLE 1. It is preferable that the lignocellulosic feedstocks employed in the method of the present invention exhibit an AX/NSP ratio of about 0.35 to about 0.45. Mixtures of lignocellulosic feedstocks which exhibit an average AX/NSP ratio of about 0.35 to about 0.45 may also be used. However, as would be evident to someone of skill in the art, a lignocellulosic feedstock or mixture of feedstocks which comprise an AX/NSP ratio or an average AX/NSP ratio outside the ranges defined above, may still be employed in the method of the present invention.

By the term "leached feedstock" it is meant a lignocellulosic feedstock which is or has been in contact with an aqueous solution for a period greater than about 2 minutes. The aqueous solution which is, or has been in contact with the leached feedstock for a period greater than about 2 minutes is termed a "leachate". A leachate may comprise dissolved substances, such as, but not limited to buffering agents' from the lignocellulosic feedstock. Further, the leachate may comprise undissolved substances, such as, but not limited to fine particles of the lignocellulosic feedstock.

By leaching the lignocellulosic feedstock the level of compounds that interfere with acid pretreatment are reduced. According to the method of the present invention, leaching comprises contacting lignocellulosic feedstock with an aqueous solution for a period between about 2 minutes and about 5 hours, preferably about 2 minutes and about 2 hours, more preferably about 10 minutes and about 30 minutes. Leaching may be performed at a temperature between about 4° C. and about 95° C., preferably between about 20° C. and 80° C. In a preferred embodiment, leaching is performed at about 60° C. to about 80° C., more preferably at about 70° C. Alternatively, leaching may be performed at a temperature over about 100° C. and under pressure.

Leaching can also recover protein from the feedstock, and this protein may be useful as an animal feed. The choice of temperature for the leaching process may therefore involve a balance between the higher leaching efficiency at high temperatures and the protein stability at lower temperature.

In a preferred embodiment, leaching reduces the amount of leachable buffering agents in the lignocellulosic feedstock from about 50% to about 100%, more preferably about 70% to about 100%, relative to the total leachable buffering agents contained in the lignocelluloic feedstock prior to the leaching step. The total leachable buffering agents in a lignocellulosic feedstock may be estimated according to Example 3.

Preferably, the aqueous solution employed in leaching lignocellulosic feedstock comprises about 0.25 to about 10 times the maximum water holding capacity per kilogram of dry lignocellulosic feedstock, more preferably about 1.5 to about 3 times the maximum water holding capacity per kilogram of dry lignocellulosic feedstock. However, leaching may be performed using an aqueous solution comprising more than about 10 times the maximum water holding capacity per kilogram of lignocellulosic feedstock. The maximum water holding capacity of a lignocellulosic feedstock may be determined by, for example, measuring the volume of water which may be absorbed by a known mass of loosely packed lignocellulosic feedstock until the point at which additional water added to the feedstock is free water. This point maybe estimated as the point wherein water forms a thin continuous layer over the lignocellulosic feedstock. In determining the maximum water holding capacity of a feedstock, it is preferable that the lignocellulosic feedstock is mechanically disrupted into particles of about the same size. Further, as would be evident to a person skilled in the art, it is preferred that the maximum water holding capacity of a feedstock be determined on a loosely packed and not tightly packed lignocellulosic feedstock. The maximum water holding capacity of a lignocellulosic feedstock may be determined as described in Example 4.

Figure 6A:
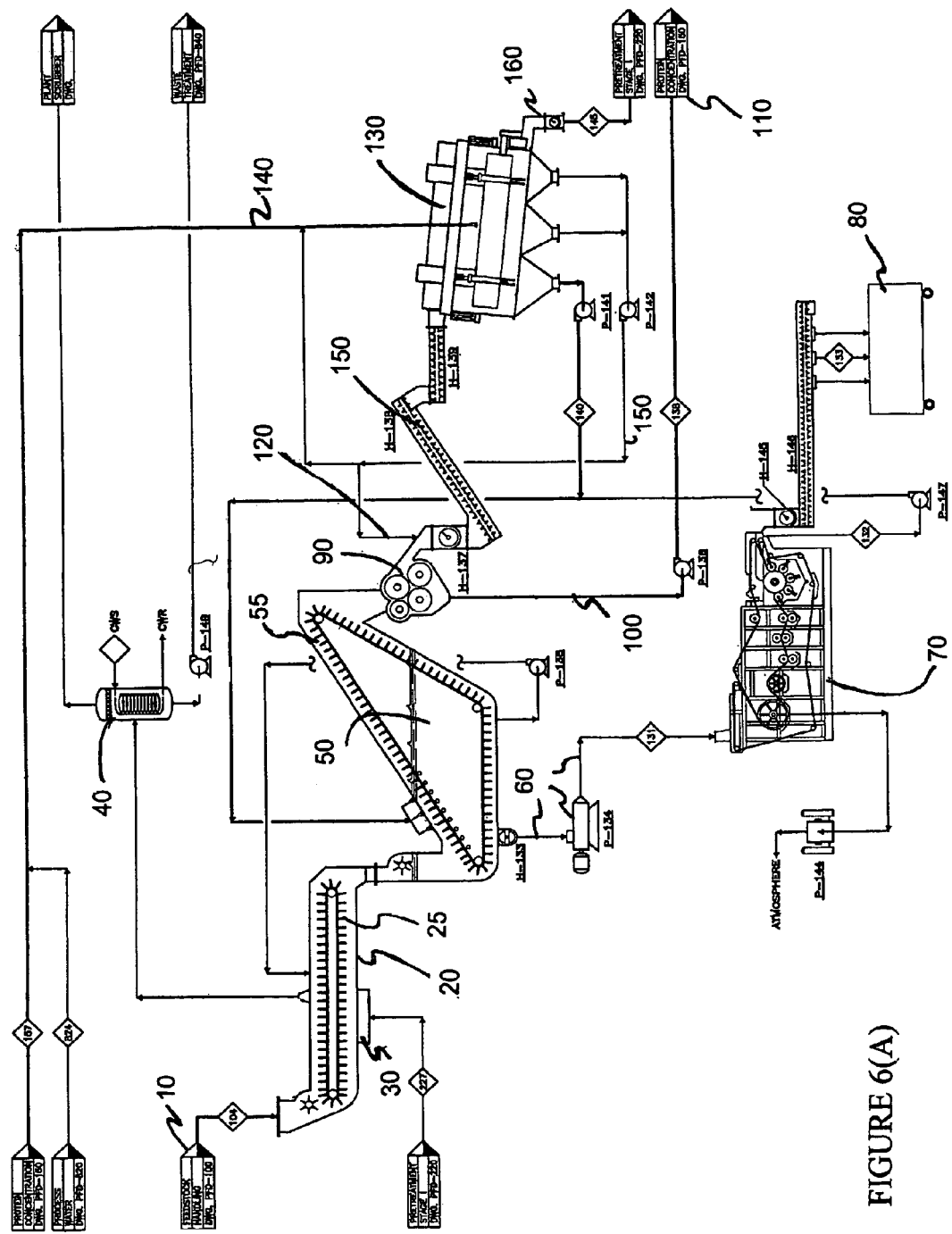
FIG. 6(A) shows an overview of an aspect of the present invention comprising a milling and leaching process.

The method of the present invention further contemplates continuous leaching of lignocellulosic feedstock. A continuous leaching process may employ a holding tank wherein a continuous feed of lignocellulosic feedstock and aqueous solution, (forming a slurry) is added to the holding tank and a continuous withdrawal of slurry is made from the holding tank. The contact time, temperature, and mass ratio of aqueous solution to feedstock are similar to that described previously for batch leaching of lignocellulosic feedstock. A non-limiting example of a continuous leaching process is shown in FIG. 6(A) and involves a two-stage countercurrent washing process. The first stage involves preconditioning of the feedstock, and the second stage comprises leaching and pressing the feedstock.

In the continuous leaching process as shown in FIG. 6(A), the milled lignocellulosic feedstock (10) is conveyed to a preconditioner (20), which consists of a moving belt (25) onto which low pressure steam (30), for example at about less than 15 psig, is sprayed to wet the fiber. The preconditioning heats the feedstock to a temperature of about 80° C. over a period of about 1 minute, that being the time the feedstock is on the belt. Volatiles in the vapour phase are removed and collected in a condenser (40).

After preconditioning, the feedstock is transferred to a leaching bath (50) where the feedstock remains submerged from about 5 to about 30 minutes, preferably about 10 to about 20 minutes. The leaching bath is where the initial leaching (leach stage 1) of the preconditioned feedstock takes place. The leaching bath tank may also be adapted for removal of sand particles and other heavy debris that may settle to the bottom of the tank. Sand and other debris may be conveyed via conveyor (60) to a sand removal press (70) and discarded in a dumpster (80).

The contents of leach bath (50) are conveyed to a roll press (90) via conveyor (55), and the feedstock crushed, to facilitate leaching and removal of liquid, and soluble components, for example but not limited to protein, salt, sugars and acids, from the solid phase. The pressate from the roll press comprising soluble protein, sugars and salts, is recovered in recovery line (100) and sent for further processing (110), for example, but not limited to protein concentration. The pressate, collected in line (150) from a second press housed within a second leach stage (130), may also be used to wash incoming feedstock in the first stage of the leach, for example at (90). The crushed fiber from the roll press (90) may be wetted with recycle leachate (120) from a second leach stage (130), and fed to a second press within (130), for example but not limited to a multi-press, via conveyor (150). The second leach stage (130), involves washing the solids with wash stream (140) and then pressing the washed solids to separate the solids from the liquid. The leached solids exit the second leach stage (130) at port (160) and are then sent for further processing as required using any process as known within the art, for example but not limited to:

ethanol production as disclosed in U.S. Pat. Nos. 6,333,181 and 5,198,074;

paper production as disclosed in U.S. Pat. Nos. 5,198,074 and 4,857,145;

biomass hydrolysis U.S. Pat. Nos. 4,556,430, 4,461,648 and 5,846,787;

sugar production as disclosed in U.S. Pat. Nos. 4,237,226 and 5,536,325 all of the above are incorporated herein by reference.

As would be evident to someone of skill in the art, lignocellulosic feedstock may be agitated during leaching, for example, but not wishing to be limiting by stirring or the like. Agitation may also occur through movement of the conveyor (55) in leach tank 50 Alternatively, leaching may be performed without agitation of the lignocellulosic feedstock.

Therefore, the present invention also provides a lignocellulosic feedstock processing system comprising, a feedstock handling device; a preconditioner capable of receiving the feedstock from the handling device, the preconditioner in communication with a steam source, the steam source for heating the feedstock, a first transfer device, for conveying the feedstock within, and from, the preconditioner to a leaching bath, a second transfer device for mixing the feedstock within the leaching bath and conveying the feedstock from the leaching bath to a press, a third transfer device for conveying pressed feedstock from the press to a second leach stage, and multi-press, to produce processed lignocellulosic feedstock.

The aqueous solution employed in the method of the present invention may comprise, but is not limited to plant water, process water, fresh water or a combination thereof. However, it is generally preferred that the aqueous solution used in the leaching of the method of the present invention comprise an aqueous solution of pH about 3 to about 9, preferably from about pH 6 to about 7, and contain less than about 10 g/L of dissolved impurities. The pH of the aqueous solution may be adjusted using any sutaible acid or base, preferably, NaOH or $H_2SO_4$ An alkaline aqueous solution may be used to help in protein extraction as outlined above.

Figure 6B:
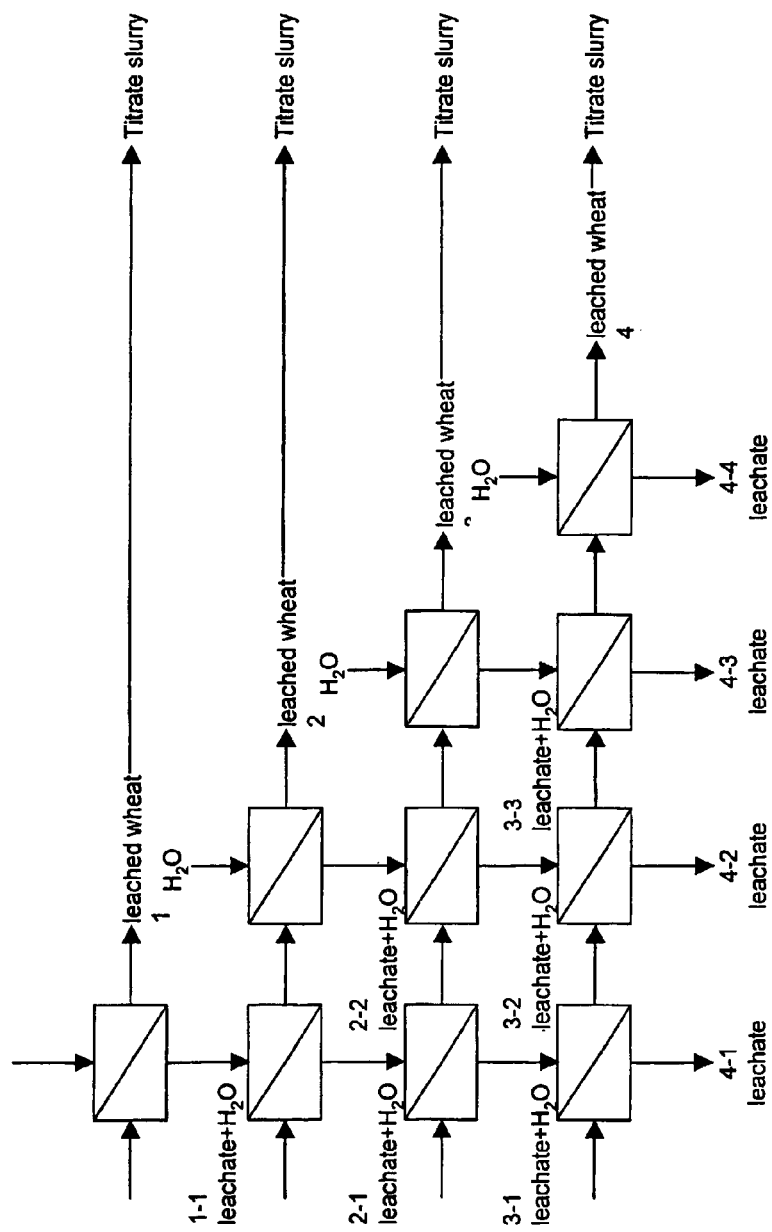
FIG. 6(B) shows a schematic representation of an aspect of the present invention comprising a multistage, countercurrent leaching process.

It is also contemplated by the method of the present invention that leaching may be performed in a plurality of stages. For example, but not wishing to be limiting, leaching may comprise from about two to about four leaching stages wherein in each stage the lignocellulosic feedstock is contacted with an aqueous solution under the conditions as defined above (e.g. see FIG. 6(B)). Following each leaching stage, the lignocellulosic feedstock is removed from the aqueous solution as discussed below.

The step of removing the leachate from the leached feedstock may be performed according to any process known in the art. For example, but not wishing to be limiting, the leachate may be removed from the leached feedstock by draining, pressing, filtering, screening, centrifuging or a combination thereof. Alternatively, but without wishing to be limiting, the leachate may be removed from the leached feedstock by rinsing or washing the leached feedstock using a washer.

As would be evident to someone of skill in the art, the step of removing the leachate from the leached feedstock need not result in complete removal of all aqueous solution from the leached feedstock. However, it is preferred that between about 20% and about 100%, preferably about 50% and about 100% of the leachate be removed from the leached feedstock.

The leachate produced in the method of the present invention may be used in processes related to or unrelated to ethanol production. Alternatively, the leachate may be discarded. Further, the leachate may be examined during or after leaching of lignocellulosic feedstock to determine the quantity of soluble components and contaminants removed from the lignocellulosic feedstock. The soluble components may include, but are not limited to buffering agents and the like. Therefore, the method of the present invention further contemplates sampling the leachate during leaching, after leaching or both before and after leaching to determine the extent of leaching of the lignocellulosic feedstock. Thus, it is possible to optimize leaching parameters such as, but not limited to, the leaching times of a lignocellulosic feedstock, or the number of leaching stages required for a lignocellulosic feedstock. Further, it is possible to monitor the extent of leaching when practicing the method of the present invention.

Following the step of removing the leachate from the leached feedstock, the feedstock may be processed using any desired method for the production of ethanol. Non-limiting examples of such methods include those described in U.S. Pat. Nos. 6,333,181; 5,198,074; 4,857,145; 4,556,430; 4,461,648; 4,237,266,5,221,537,5,536,325; 5,628,830; 5,846,787 (which are incorporated herein by reference).

A preferred method to further process the leached feedstock comprises the step of acidifying the leached feedstock to a pH between about 0.5 and about 8, preferably, a pH of about 0.5 to about 3 to produce an acidified feedstock. The leached feedstock may be acidified using any acid known in the art, but is preferably acidified using sulfuric acid, nitric acid or hydrochloric acid. In a preferred embodiment the acid is sulfuric acid.

Reacting acidified feedstock under conditions which disrupt fiber structure as contemplated in the method of the present invention, may be performed according to any method known in the art, for example, but not limited to pretreatment by steam explosion as described in U.S. Pat Nos. 4,461,648, and 4,237,226 which are herein incorporated by reference. Further, any parameters used in the prior art to effect steam explosion pretreatments, such as, but not limited to those described in Foody, et al, Final Report, *Optimization of steam Explosion Pretreatment*, U.S. DEPARTMENT OF ENERGY REPORT ET230501 (April 1980, which is herein incorporated by reference) maybe used in the method of the present invention.

Preferably, the step of reacting the acidified feedstock is performed using a temperature between about 100° C. to about 220° C. at about pH 0.5 to about 2.5 for about 5 seconds to about 60 minutes. It is understood by those skilled in the art that the feedstock temperature is that of the feedstock itself, which might differ from the temperature measured outside the reaction chamber. Devices used to carry out this pretreatment include, but are not limited to sealed batch reactors, continuous extruders and steam guns.

It is also within the scope of the present invention that a two-stage pretreatment process may be used, whereby the first stage improves the cellulose hydrolysis somewhat while solubilizing primarily the hemicellulose but little cellulose. The second stage then completes a full pretreatment. In this embodiment, the first stage reaction is run at a temperature of less than about 180° C. while the second stage reaction is run at a temperature of greater than about 180° C. Preferably, the first stage of the reaction is carried out at a temperature of about 60° C. to about 140° C. for 0.25 to 24 hours at pH 0.5 to 2.5. More preferably, the first stage of pretreatment is carried out at a temperature of 100° C. to 130° C. for 0.5 to 3 hours at pH 0.5 to 2.5. While the second stage of reaction may be carried out at a temperature of 180° C. to 270° C., at pH 0.5 to 2.5 for a period of 5 seconds to 120 seconds. The two-stage pretreatment provides separate recovery of the hemicellulose for downstream processing.

Reacting the acidified feedstock as contemplated by the method of the present invention, produces a composition comprising xylose and a pretreated feedstock. Preferably, as a result of the methods as described herein, the composition comprises between about 150 to about 260 mg of xylose per gram of dry lignocellulosic feedstock. As will be evident to someone of skill in the art, the composition may comprise sugars other than xylose and a variety of other components. The xylose may be purified from the composition.

The composition or pretreated feedstock derived from practicing the method of the present invention may be treated With cellulase enzymes to hydrolyse cellulose to glucose using methods as would be known to one of skill in the art. A cellulase enzyme treatment may be performed by mixing the pretreated feedstock or composition derived from the method of the present invention with water and titrating the mixture to a pH of about 5 to achieve a slurry of 5% to 10% by weight cellulose. Cellulase enzymes are then added to the mixture. Typically, the hydrolysis is run for about 24 to about 200 hours at about 50° C. At the end of the hydrolysis, glucose and other water soluble sugars remain dissolved in solution, while unconverted cellulose, lignin, and other insoluble portions of the substrate remain in suspension or precipitate from solution. A syrup comprising glucose and other dissolved sugars and solutes may be recovered by filtering the hydrolysis slurry. Washing of the fiber solids may also be performed to increase the yield of glucose and other sugars.

It is also contemplated that glucose produced by the hydrolysis of cellulose from the pretreated feedstock may be fermented to ethanol. Fermentation of glucose and other sugars to ethanol may be performed by conventional processes known to those skilled in the art, and may be effected by a variety of microorganisms including yeast and bacteria or genetically modified microorganisms, for example, but not limited those described in WO95/13362, WO97/42307 and the article entitled Alcohol production from Cellulosic Biomass: The Iogen Process in: The Alcohol Textbook.(2000, Nottingham University Press) which are herein incorporated by reference).

It is also contemplated that both glucose and xylose produced in the method of the present of the present invention may be fermented to ethanol. Alternatively, xylose and glucose maybe fermented to ethanol independently. Ethanol production and recovery are performed by well-established processes used in the alcohol industry.

Thus, the present invention, provides a method of producing ethanol from a lignocellulosic feedstock comprising,
- a) leaching the lignocellulosic feedstock by contacting the feedstock with at least one aqueous solution for a period greater than about 2 minutes to produce a leached feedstock and a leachate;
- b) removing the leachate from the leached feedstock;
- c) acidifying the leached feedstock to a pH between about 0.5 and about 3 to produce an acidified feedstock, and;
- d) reacting the acidified feedstock under conditions which disrupt fiber structure and hydrolyze a portion of hemicellulose and cellulose of the acidified feedstock, to produce a composition comprising xylose and a pretreated feedstock;
- e) treating the composition comprising xylose and pretreated feedstock with cellulase under conditions which hydrolyse cellulose in the pretreated feedstock to glucose, producing a sugar solution comprising xylose and glucose, and;
- f) either:
  - i) fermenting the sugar solution to ethanol;
  - ii) treating the composition with a microorganism under conditions which permit fermentation of the xylose in the composition to ethanol; or
  - iii) separating the pretreated feedstock form the composition, and treating the pretreated feedstock with cellulase under conditions which hydrolyse cellulose in the pretreated feedstock to glucose, producing a sugar solution comprising glucose, and fermenting the sugar solution to ethanol.

Thus, it is contemplated that xylose produced in the pretreatment of lignocellulosic feedstock may be fermented in combination with glucose, or separate from glucose produced by cellulose hydrolysis of the pretreated feedstock.

It is also contemplated that the glucose may be fermented to lactic acid or converted to other useful products such as, but not limited to sorbitol, acetic acid, citric acid, ascorbic acid, propanediol, butanediol, acetone, butanol, or a combination thereof.

Leaching of lignocellulosic feedstock as performed in the method of the present invention reduces the amount of acid required in a hydrolysis process compared to lignocellulosic feedstock which has not been subjected to leaching. Referring now to FIG. 1, there is shown the amount of acid required to titrate water to a desired pH (dashed line) relative to the amount of acid required to titrate a leachate solution (solid line) comprising an aqueous solution which has been in contact with a lignocellulosic feedstock according to the method of the present invention. The data from FIG. 1 indicate that lignocellosic feedstocks comprise buffering agents may be removed from the feedstock by leaching with aqueous solution. Removing all or a portion of the buffering agents from a lignocellulosic feedstock reduces the amount of acid that must be used in a dilute acid prehydrolysis process such as, but not limited to steam explosion.

Figure 2:
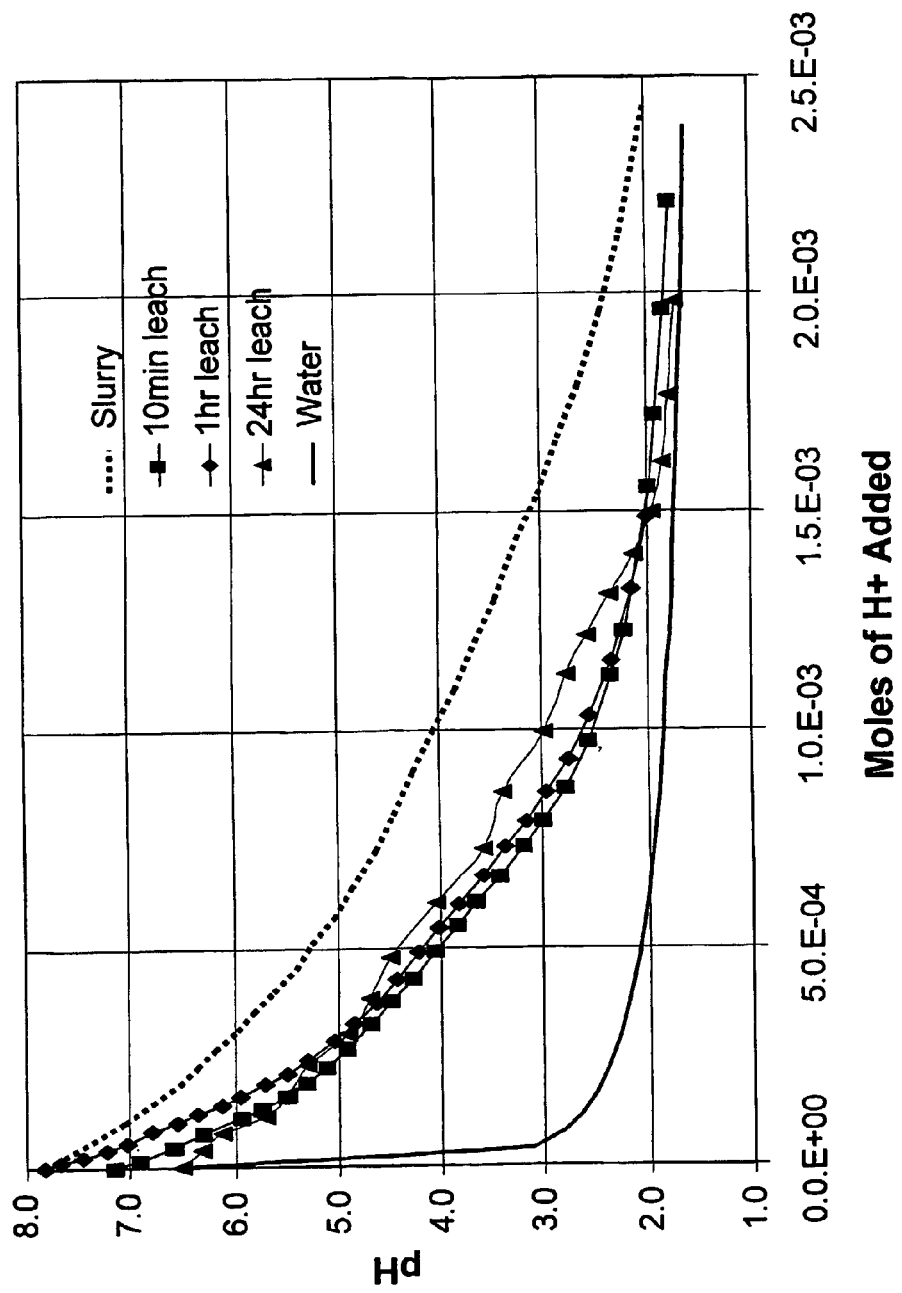
FIG. 2 shows a graphical representation depicting the amount of acid required to titrate water (solid line), a slurry of lignocellulosic feedstock and water (dashed line), and three leachates which are produced by leaching lignocellulosic feedstock for 10 minutes (filled squares), 1 hour (filled diamonds) and 24 hours (filled triangles).

Referring now to FIG. 2, there is shown the amount of acid required to titrate water, an unleached lignocellulosic feedstock slurry, or three leachates which have been used to contact three lignocellulosic feedstocks for a period of 10 minutes, 1 hour or 24 hours, respectively. The results shown in FIG. 2 suggest that leaching lignocellulosic feedstock for a period between about 10 minutes and about 24 hours is capable of removing buffering agents from the feedstock so as to reduce the amount of acid required to titrate the pH of the leached lignocellulosic feedstock.

Figure 3:
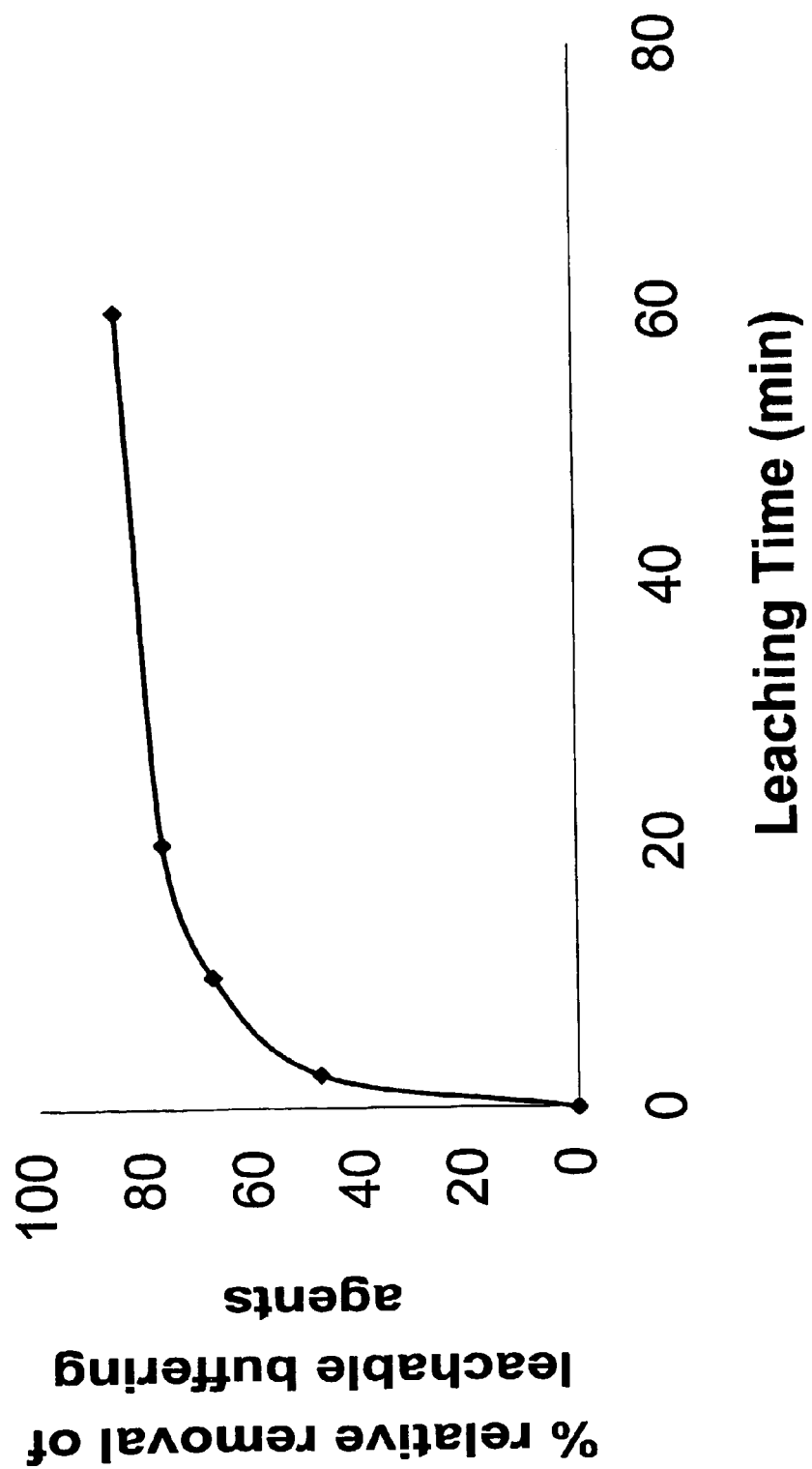
FIG. 3 shows a graphical representation of the effect of leaching time on the percent alkalinity removal relative to a thoroughly leached feedstock.

Referring now to FIG. 3, there is shown the percent alkalinity removal as a function of leaching time for a lignocellulosic feedstock relative to a thoroughly leached feedstock prepared according to Example 4. The results shown in FIG. 3 suggest that a leaching time of about 2 minutes is capable of leaching about 48% of the total leachable buffering agents from the lignocellulosic feedstock and a time of about 60 minutes leaches about 85% of the total leachable buffering agents.

Figure 4:
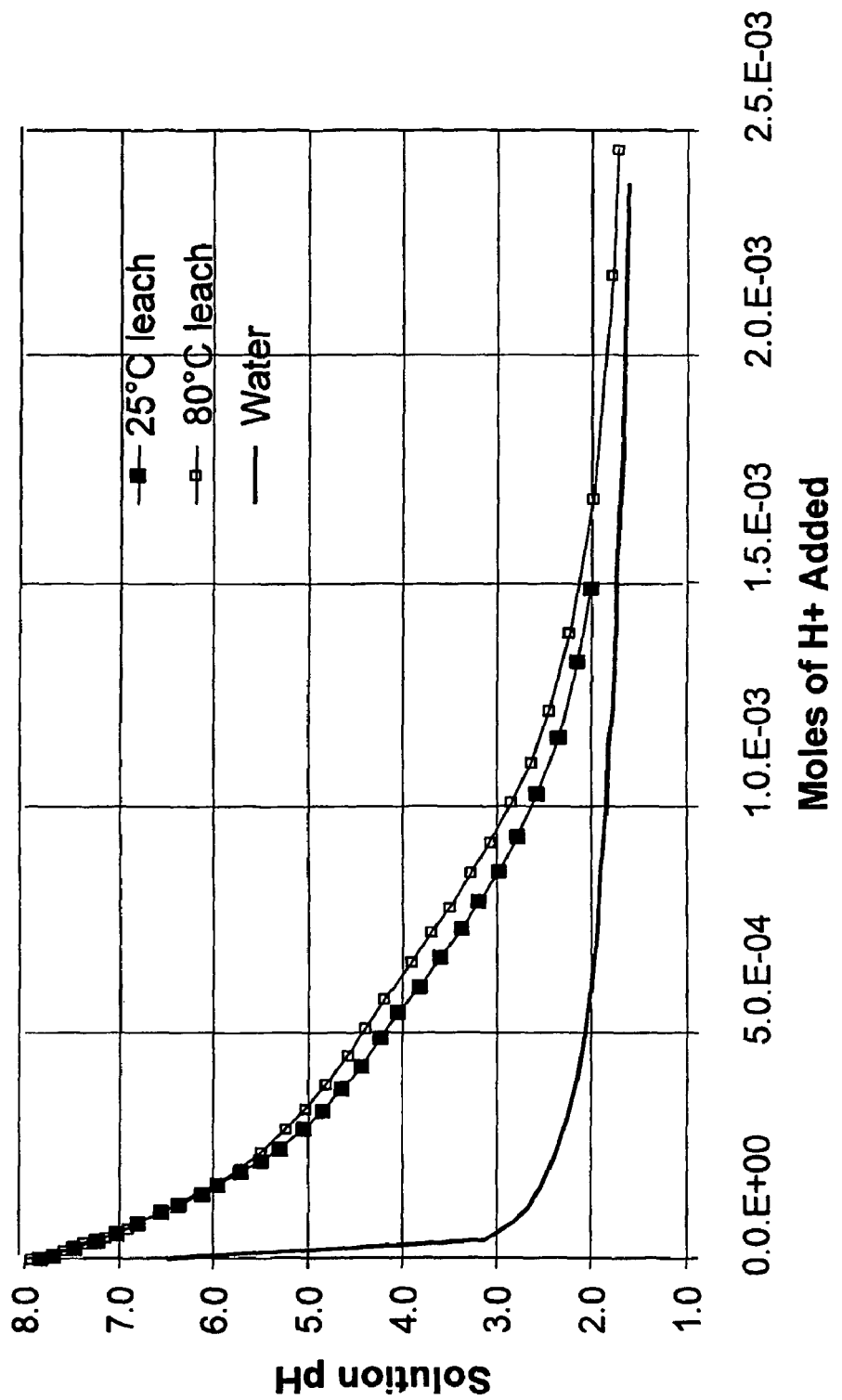
FIG. 4 shows a graphical representation showing the amount of acid required to titrate water (solid line), a leachate derived from leaching lignocellulosic feedstock at 25° C. (filled squares) and a leachate derived from leaching lignocellulosic feedstock at 80° C. (open squares).

Referring now to FIG. 4 there is shown the effect of temperature on leaching of lignocellulosic feedstock. These data indicate that leaching of lignocellulosic feedstock may be performed under a wide range of temperatures. Specifically, lignocellulosic feedstock treated by leaching at temperatures between about 25° C. and about 80° C. produce leachates comprising buffering agents. Removal of buffering agents from lignocellulosic feedstocks during leaching produces leached feedstock which requires less acid load to titrate the feedstock to an acidic pH suitable for dilute acid prehydrolysis processes such as, but not limited to, steam explosion. While the results shown in FIG. 4 suggest that leaching temperatures of between about 25° C. and about 80° C. may be used in the method of the present invention, other temperatures outside this range may also be used in the method of the present invention.

Figure 5:
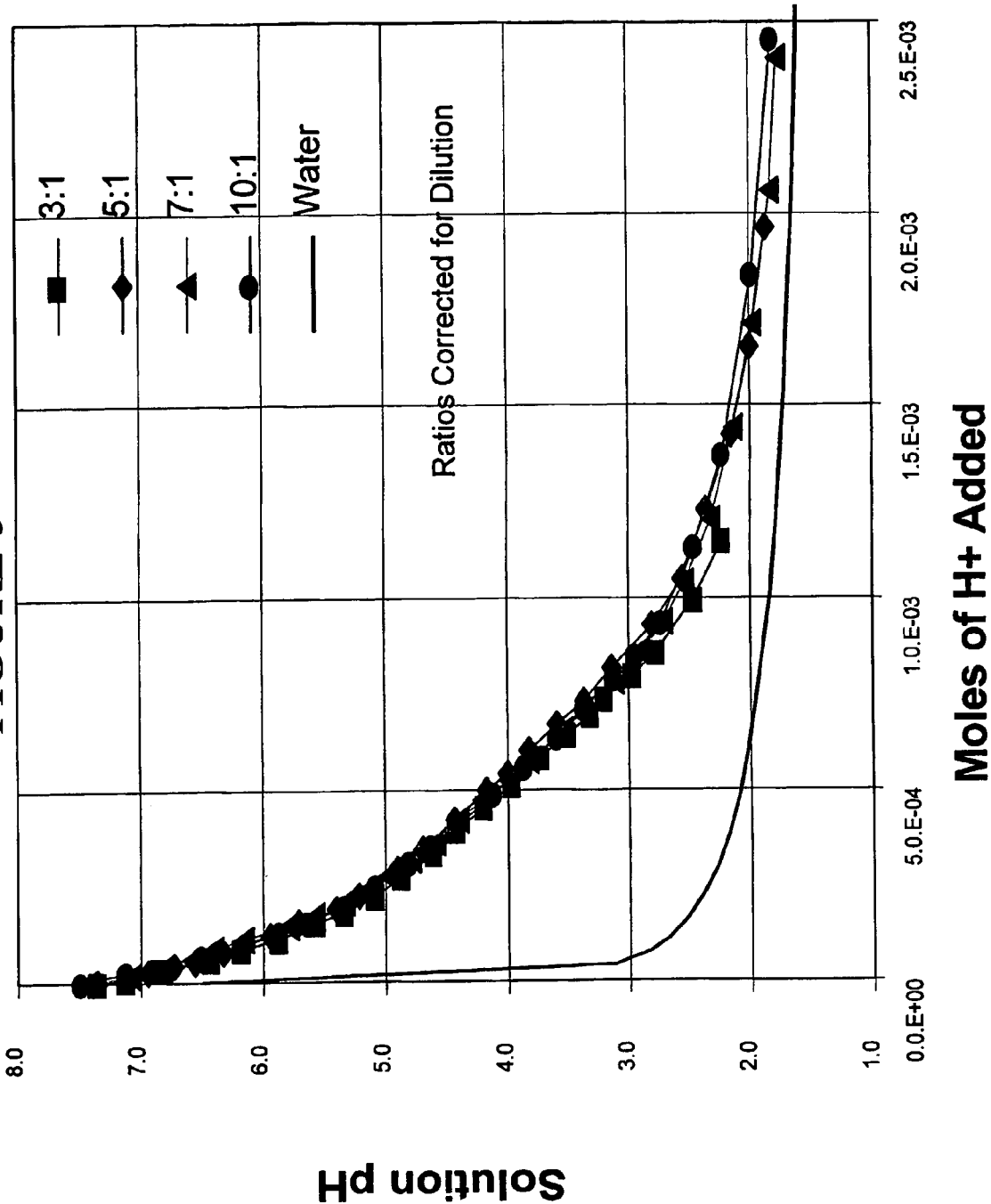
FIG. 5 shows a graphical representation depicting the amount of acid required to titrate water (solid line) and four leachates derived from leaching lignocellulosic feedstock using a mass ratio of water to dry lignocellulosic feedstock of about 3:1 (filled squares), 5:1 (filled diamonds), 7:1 (filled triangles), and 10:1 (filled circles).

Referring now to FIG. 5, there is shown the amount of acid required to titrate leachates, wherein the mass ratio of aqueous solution (leachate) to dry lignocellulosic feedstock to is about 3:1, 5:1, 7:1 and 10:1. The results depicted in FIG. 5 are corrected for volume and suggest that a wide range of leachate to feedstock ratios may remove similar amounts of buffer agents from lignocellulosic feedstocks. The minimum ratio of aqueous solution to lignocellulosic feedstock corresponds to an amount about equal to or greater than the maximum water holding capacity of the feedstock.

The results depicted in FIGS. 1-5 are based on a single leaching of lignocellulosic feedstock. However, the method of the present invention also contemplates multiple teachings of lignocellulosic feedstock. For example, but not to be considered limiting, lignocellulosic feedstock may be subjected to multiple leaching stages, wherein after each leaching, the leachate is removed from the leached feedstock as described previously herein. In embodiments of the method of the present invention wherein multiple teachings of the lignocellulosic material are performed, preferably the method comprises between about 2 and about 4 leachings of the lignocellulosic feedstock. Without wishing to be bound by theory, multiple teachings may allow the volume of aqueous solution per mass of lignocellulosic feedstock to be reduced in practicing the method of the present invention.

The method of the present invention further contemplates multiple teachings of lignocellulosic feedstock wherein the multiple teachings are performed in a countercurrent fashion. Referring now to FIG. 6, there is shown a 1-4 stage countercurrent leaching process which may be employed in the method of the present invention. FIG. 6 is provided as an example and is not intended to be limiting in any manner. As shown in FIG. 6, a first lignocellulosic feedstock is leached with water in a first leaching stage to produce a first leachate and a first leached feedstock. Following the appropriate leaching time, the first leachate is separated from the first leached feedstock. This represents a one stage leaching of lignocellulosic feedstock.

As further shown in FIG. 6, the first leachate or an aliquot thereof may be used to leach a second lignocellulosic feedstock thereby producing a second leachate and a second leached feedstock. The second leachate, or an aliquot thereof, may be used to leach a third lignocellulosic feedstock. Also shown in FIG. 6, the second leached feedstock is further leached with water in a second leaching stage. The leachate produced in this second leaching may be used to leach a further lignocellulosic feedstock which has been previously leached or unleached. The entire process maybe repeated for any number of stages. However, in embodiments of the present invention which employ multiple teachings of lignocellulosic feedstock, it is preferred that 2 to 4 leaching stages are used. Further, although FIG. 6 represents a countercurrent leaching process, wherein a leachate from a first leaching is employed in the leaching of a second lignocellulosic feedstock, it is also contemplated that each leaching may be performed with an aqueous solution that was not previously used to leach lignocellulosic feedstock.

In embodiments of the method of the present invention wherein multiple teachings of lignocellulosic feedstock are performed in a countercurrent manner, it is preferred that a subsequent leaching of a lignocellulosic feedstock employ an aqueous solution containing less impurities than a previous leaching of the same lignocellulosic feedstock, as would be known to someone of skill in the art. More preferably, the last leaching of a multiple leaching process comprises substantially pure water, that is water that has not been previously used to leach a feedstock.

Figure 7:
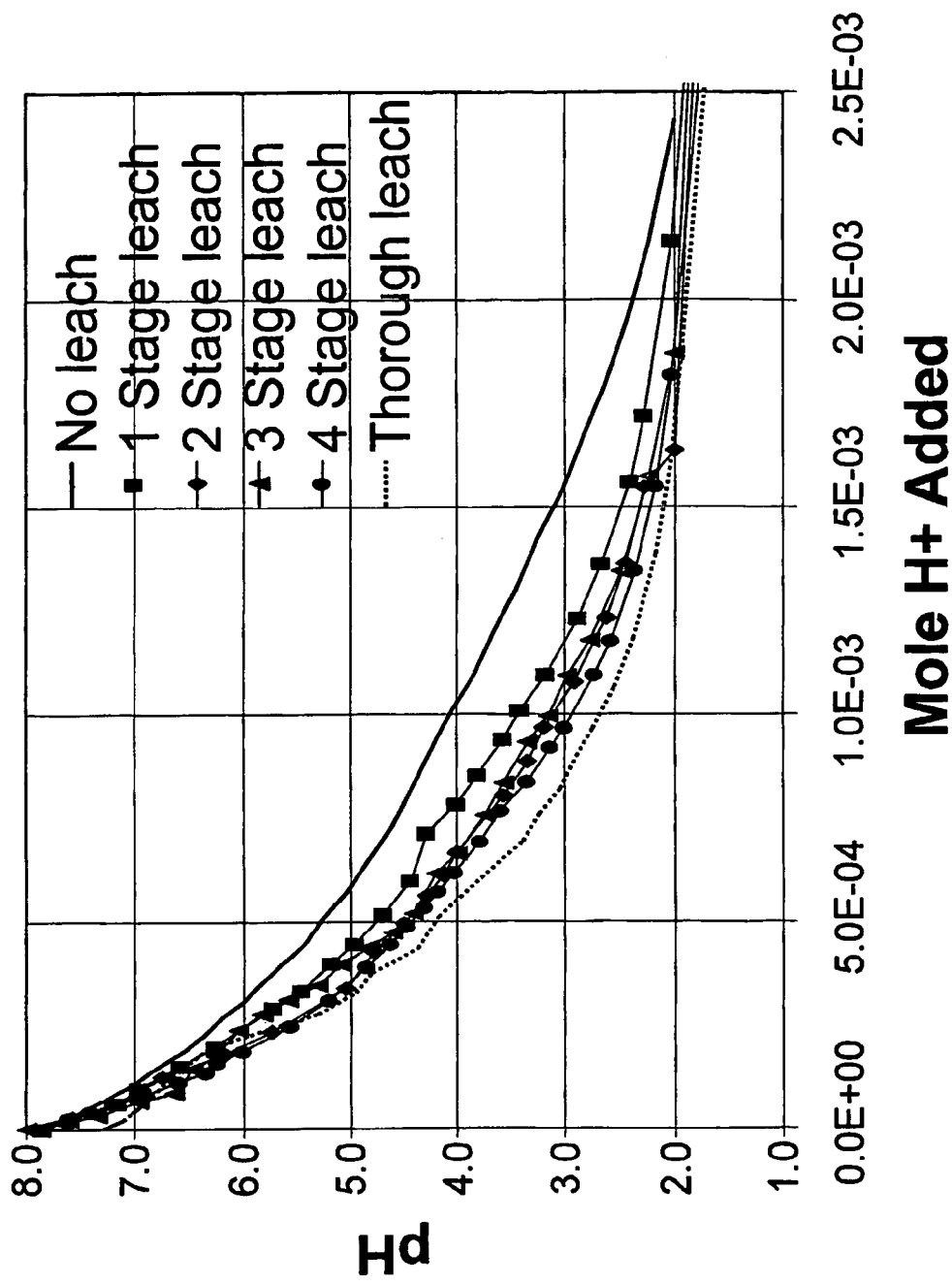
FIG. 7 shows a graphical representation depicting the amount of acid required to titrate unleached lignocellulosic feedstock (solid line), thoroughly leached lignocellulosic feedstock (dashed line), a leachate derived from a single leaching process (filled squares), a leachate derived from a two-stage leaching process (filled diamonds), a leachate derived from a 3 stage leaching process (filled triangles) and a leachate derived from a four stage leaching process (filled circles).

Referring now to FIG. 7, there is shown the amount of acid required to titrate an unleached lignocellulosic feedstock, four leached lignocellulosic feedstocks comprising between 1 and 4 teachings and a thoroughly leached lignocellulosic feedstock The results shown in FIG. 7 suggest that multiple teachings of lignocellulosic feedstock may be used to remove buffering agents from the feedstock thereby reducing the acid load required for dilute acid prehydrolysis processes, for example, but not limited to steam explosion. Thus, the method of the present invention contemplates multiple leachings of lignocellulosic feedstock. In a preferred embodiment, the present invention contemplates from about 1 to about 5 Teachings of lignocellulosic feedstock wherein the volume of aqueous solution is about 3 to about 10 times the volume of the maximum water holding capacity per kilogram of the lignocellulosic feedstock, more preferably about 7 times the maximum water holding capacity of the lignocellulosic feedstock.

The results depicted in FIGS. 1-7 suggest that leaching of lignocellulosic feedstock may reduce the amount of acid required to titrate the pH of the leached feedstock to a value suitable for a dilute-acid hydrolysis. Thus, the present invention further contemplates a method of reducing the amount of acid required to effect dilute acid hydrolysis treatment of lignocellulosic feedstock. Further, leaching of lignocellulosic feedstock may be used to reduce the amount of acid required in other processes such as, but not limited to those processes employing acid to depolymerize cellulose to glucose. Thus, the present invention contemplates a method of reducing the amount of acid required to effect acid depolymerization of cellulose to glucose.

Leaching of lignocellulosic feedstock is capable of removing buffering agents from the feedstock. Thus, leaching lignocellulosic feedstock may be employed to reduce the amount of base required to titrate the pH of the lignocelluloic feedstock to an appropriate pH for other processes, such as but not limited to ammonia pretreatment of lignocellulosic feedstock. The present invention contemplates a method of reducing the amount of base required to effect an ammonia pretreatment of lignocellulosic feedstock.

Xylose Production

A drawback of dilute acid prehydrolysis processes known in the art is that these processes destroy xylose during treatment. The destruction of xylose during dilute acid prehydrolysis reduces the ethanol yield that may be obtained from the feedstock.

Figure 8A:
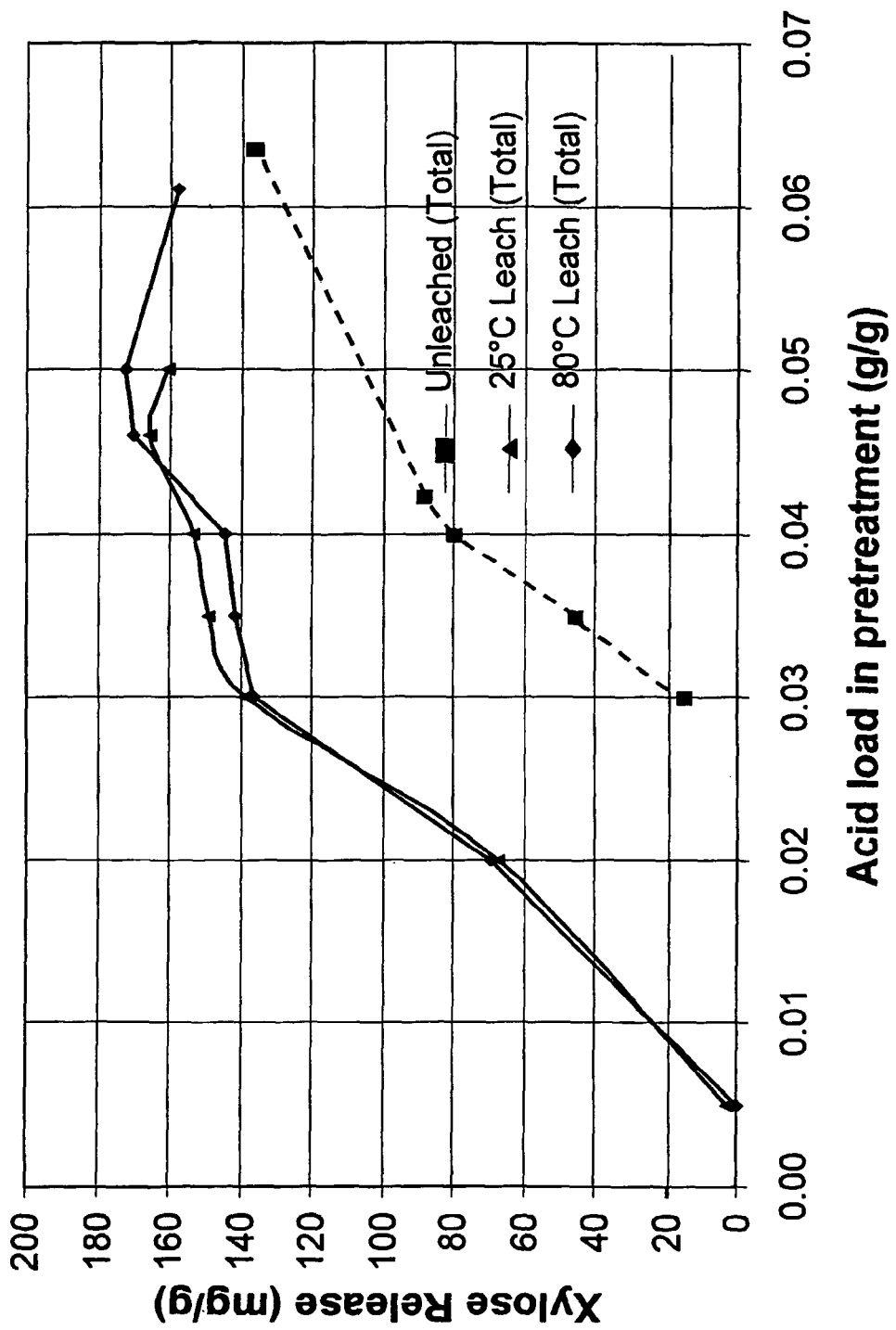
FIG. 8(A) shows a graphical representation depicting total xylose polymer plus monomer release from lignocellulosic feedstock as a function of acid pretreatment load for an unleached lignocellulosic feedstock (open squares), a lignocellulosic feedstock treated by leaching at room temperature (open triangles), and a lignocellulosic feedstock treated by leaching at 80° C. (open diamonds).

Referring now to FIG. 8(A), there is shown the amount of xylose polymer released from lignocellulosic feedstock as a function of acid load in a dilute-acid pretreatment process. As shown in FIG. 8(A), leaching of lignocellulosic feedstock prior to dilute acid pretreatment results in a higher amount of xylose polymer release from lignocellulosic feedstock than does unleached lignocellulosic feedstock treated in an identical manner. Furthermore, the amount of xylose released from pretreated feedstock is greater than the unleached feedstock for any given amounts of acid used during pretreatment, and the amount of acid required to effect xylose release is much less than that of the unleached feedstock.

Figure 8B:
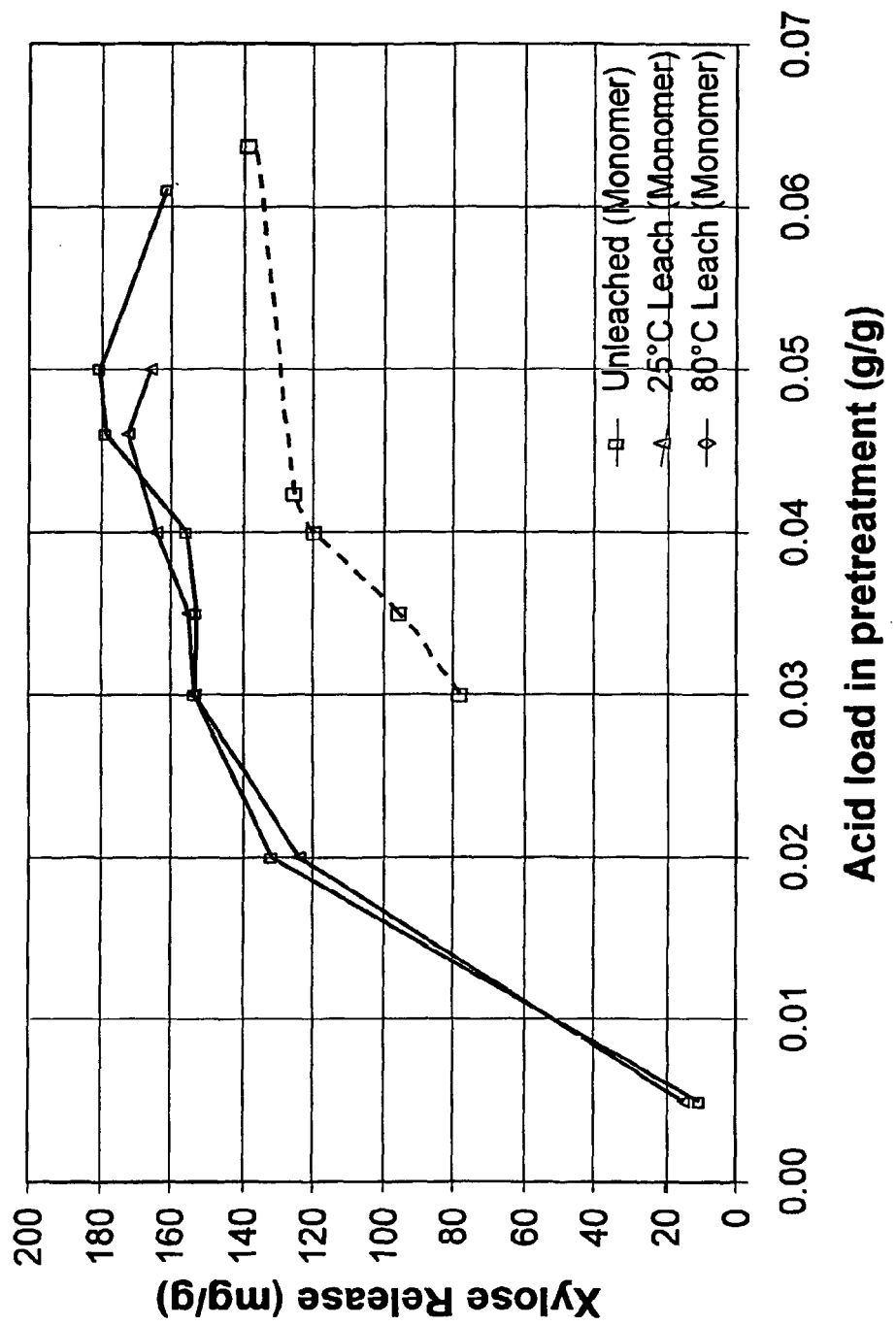
FIG. 8(B) shows a graphical representation depicting xylose monomer release from lignocellulosic feedstock as a function of acid pretreatment load for an unleached lignocellulosic feedstock (filled squares), a lignocellulosic feedstock treated by leaching at room temperature (filled triangles), and a lignocellulosic feedstock treated by leaching at 80° C. (filled diamonds).

Referring now to FIG. 8(B), there is shown the amount of xylose monomer released from lignocellulosic feedstock as a function of acid load in a dilute-acid pretreatment process. As shown in FIG. 8(B), leaching of lignocellulosic feedstock prior to dilute acid pretreatment results in a higher amount of xylose monomer release from lignocellulosic feedstock than does unleached lignocellulosic feedstock treated in an identical manner. Again, the amount of xylose released from pretreated feedstock is greater than the unleached feedstock for any given amount of acid used during pretreatment. The amount of acid required to effect xylose release is also much less than that of the unleached feedstock.

Therefore, the method of the present invention increases the amount of xylose released from lignocellulosic feedstocks following dilute acid prehydrolysis processes and increases ethanol yield when the same feedstock is treated with microorganisms, cellulase enzyme, or both, and subsequently fermented to ethanol.

The above description is not intended to limit the claimed invention in any manner, Furthermore, the discussed combination of features might not be absolutely necessary for the inventive solution.

The present invention will be further illustrated in the following examples. However, it is to be understood that these examples are for illustrative purposed only, and should not be used to limit the scope of the present invention in any manner.

EXAMPLES

Example 1

MEASUREMENT OF AX/NSP IN FEEDSTOCKS

The ratio of arabinan plus xylan to total non-starch polysaccharides of a given feedstock is determined based on a compositional analysis of the feedstocks. This analysis is performed, as follows:

Feedstocks examined include barley straw, wheat straw, wheat chaff, oat hulls, switch grass, corn stover, maple wood, pine wood, and three varieties of corn cobs. All are obtained locally in Ottawa, Ontario except the oat hulls, which are from Quaker Oats in Peterborough, Ontario. The feedstocks are coarsely ground in a Waring blender and then milled through a #20 mesh screen using a Wiley mill. The feedstocks are stored at ambient temperature in sealed bags until the time of use. The moisture content of small samples is 5% to 10% and is determined by drying at 100° C.

Approximately 0.2 grams of sample is weighed into test tubes, each containing 2.5 ml of 72% sulfuric acid. The tubes are vortex mixed, capped, and placed in a 40° C. water bath for 30 minutes, with vigorous vortex mixing every 10 minutes. After the 30 minute incubation, the tube contents are transferred into preweighed 250 ml flasks containing 97.5 ml deionized water, which reduced the acid content to 1.8%. Each flask is transferred to a steam autoclave and is maintained at 121° C. for 1 hour. The flask is weighed after autoclaving Yellow Springs Instrument (YSI) glucose analyzer and used to determine the starch concentration of the feedstock, taking into account the water necessary to hydrolyse the starch.

The protein and ash content of the feedstocks are determined by standard Kjeldahl nitrogen and ash oven methods.

The lignin content of the samples is determined by measuring the amount of insoluble solids remaining after the sulfuric acid treatment of the feedstocks, then subtracting the amount of ash present.

The results of these measurements are shown in TABLE 1. The material recovered is between 849 and 1018 mg per gram of original solids (mg/g). This corresponds to 84.9%, by weight, to 101.8% of the starting material, which is typical mass balance closure in these systems.

TABLE 1

COMPOSITION OF THE FEEDSTOCKS
Measured composition (mg/g)

| Feedstock | Glucan | Starch | Xylan | Arabinan | Lignin | Ash | Protein | Total |
|---|---|---|---|---|---|---|---|---|
| Barley Straw | 426 | 19.6 | 161 | 28 | 168 | 82 | 64 | 929 |
| Wheat Straw | 349 | 12 | 167 | 18 | 204 | 83 | 64 | 885 |
| Wheat chaff | 405 | 14.4 | 200 | 36 | 160 | 121 | 33 | 955 |
| Switch grass | 331 | 3.4 | 212 | 24 | 183 | 48 | 54 | 852 |
| Corn stover | 370 | 2.3 | 189 | 22 | 127 | 60 | 81 | 849 |
| Maple wood | 504 | 4 | 150 | 5 | 276 | 6 | 6 | 947 |
| Pine wood | 649 | 1 | 33 | 14 | 320 | 0 | 2 | 1018 |
| Corn cobs (red) | 436 | 34 | 253 | 38 | ND (2) | ND | ND | ND |
| Corn cobs (white) | 439 | 28 | 250 | 38 | ND | ND | ND | ND |
| Corn cobs (Indian) | 438 | 8.5 | 240 | 36 | ND | ND | ND | ND |
| Oat Hulls | 436 | 90 | 187 | 26 | 170 | 44 | 38 | 901 |
| Soybean Stover | 377 | ND | 120 | 13 | ND | ND | ND | ND |

(1) Total = Glucan + Xylan + Arabinan + Lignin + Ash + Protein
(2) ND = Not determined The concentrations of glucose, xylose, and arabinose present in the filtrates are measured by using a Dionex Pulse-Amperometric HPLC. These measurements are then related to the weight of the initial sample of feedstock present and expressed as glucan, xylan, and arabinan contents, respectively, of the feedstock, with small adjustments to take into account (1) the water of hydration to make the monomers from polymers and (2) the amount of material destroyed by the concentrated acid, which is measured by taking pure cellulose, xylose, and arabinose controls through the procedure. The determination is performed in triplicate and the average value is reported.

The cellulose content is determined by subtracting the starch content from the total glucan. The starch content is determined by adding 1 gram of Wiley-milled feedstock to a 250 ml flask containing 20 ml of deionized water, 0.2 ml of 91.7 g/L $CaCl_2.2H_2O$ stock solution, and 50 microliters of a 1:100 solution of Sigma Alpha Amylase #A3403 in deionized water. Each flask is adjusted to pH 6.4 to 6.6 using dilute sodium hydroxide, then incubated in a boiling water bath for one hour. The flasks are incubated for 30 minutes in a steam autoclave at 121° C. after the addition of a second 50 µl dose of amylase. Finally, the flask is incubated for another 60 minutes in the boiling water bath with a third 50 µl dose of amylase. The flasks are then cooled to ambient temperature and adjusted to pH 4.2 to 4.4 using dilute hydrochloric acid. A 0.5 ml aliquot of Novo Spritamylase stock solution is added; the stock solution consisted of 3 grams of enzyme solution in 100 ml deionized water. The flasks are shaken at 50° C. for 20 hours with 150 RPM agitation. The flasks are then cooled and the contents are filtered over glass microfiber filter paper. The glucose concentration is then measured on a The AX/NSP content of the feedstocks is shown in TABLE 2. Of the 12 feedstocks analyzed, eight have AX/NSP of greater than about 0.35. These include the samples of wheat straw, wheat chaff, switch grass, corn stover, oat hulls and corn.

TABLE 2

AX/NSP COMPOSITION OF THE FEEDSTOCKS

| Feed-stock | Cellulose (mg/g) (1) | AX (mg/g) (2) | NSP (mg/g) (3) | AX/NSP |
|---|---|---|---|---|
| Barley Straw | 407 | 189 | 596 | 0.317 |
| Wheat Straw | 337 | 185 | 522 | 0.354 |
| Wheat chaff | 391 | 236 | 627 | 0.376 |
| Switch grass | 328 | 236 | 564 | 0.418 |
| Corn stover | 347 | 211 | 558 | 0.378 |
| Maple wood | 500 | 155 | 655 | 0.237 |
| Pine wood | 648 | 47 | 695 | 0.068 |
| Corn cobs (red) | 402 | 291 | 693 | 0.42 |
| Corn cobs (white) | 411 | 288 | 699 | 0.412 |
| Corn cobs (Indian) | 429 | 276 | 705 | 0.391 |
| Oat Hulls | 346 | 213 | 559 | 0.381 |
| Soybean Stover | 377 | 133 | 510 | 0.26 |

(1) Cellulose = Glucan − Starch
(2) AX = Xylan + Arabinan
(3) NSP = Xylan + Arabinan + Cellulose

Example 2

Leaching and Dilute Acid Pretreatment of Lignocellulosic Feedstock

A. Leaching

Wheat straw is ground using a Wiley mill to produce particles of a size less than 20 mesh. The milled lignocellulosic feedstock is added to water at 25° C. or 80° C. for leaching. For comparative purposes an equivalent amount of Wiley milled straw is set aside as a control and processed without leaching. Leaching of the lignocellulosic feedstock is performed for 60 minutes using a mass ratio of water to lignocellulosic feedstock of 10:1. Following leaching, the leached lignocellulosic material is filtered and pressed to 50% solids content.

B. Dilute Acid Hydrolysis of Leached Feedstock

The leached lignocellulosic material (1.0 grams, total fiber) is placed in a 10 mL stainless steel reactor. A volume of 5% sulfuric acid is added to the leached feedstock to obtain a ratio of acid to leached feedstock in the range of 0.5% to 6.3% weight/weight. The reactor is sealed and placed in a 200° C. oil bath for 2 minutes. Following the 5 minute incubation the reactor is placed in cold water to quench the reaction.

C. Determination of Xylose Concentration

The xylose concentration of the treated feedstock is measured by filtering an aliquot and hydrolysing the sample at 120° C. with 2% sulfuric acid. The xylose concentration of the hydrolysate is measured by HPLC and is expressed in milligrams of xylose per gram of lignocellulosic feedstock.

The results obtained for xylose release from lignocellulosic feedstock treated according to the method of the present invention are shown in FIGS. 8A and 8B. The highest xylose yield obtained with 25° C. leaching was about 170 mg/g, representing an improvement of about 20% over lignocellulosic biomass that is not subjected to leaching prior to pretreatment. An acid load of about 4.5% on the feedstock is required to reach this yield. An acid load of about 2.5% is required to produce 140 mg/g xylose according to the method of the present invention. Without leaching, a similar process requires about 6.5% acid load performed under the conditions described above.

D. Leaching Time

Experiments in which leaching time is varied are performed in a similar manner as those described above, except that the leaching times are 2 minutes, 10 minutes, 1 hour and 24 hours. The results of varying the leaching time are shown in FIGS. 2 and 3.

E. Leaching Temperature

Experiments in which the leach temperature is varied are performed in a similar manner as those described above, except that the leaching temperatures are 25° C. and 80° C. The results of varying the leaching temperature are shown in FIG. 4.

F. Ratio of Lignocellulosic Feedstock to Water Ratio

Experiments in which the mass ratio of water (leachate) to lignocellulosic feedstock (leachate) is varied are performed in a similar manner as those described above, except that the mass ratio of water to lignocellulosic feedstock to water is 3:1, 5:1, 7:1 and 10:1. The results of these Teachings are shown in FIG. 5.

G. Multiple Leaching Stages

The leaching stage is performed in a similar manner with a mass ratio of water to lignocellulosic feedstock of about 5:1. Leaching is performed for 10 minutes at 25° C., followed by pressing the leached lignocellulosic feedstock to 50% solids (mass ratio of water to feedstock of about 0.5:1. Additional leaching stages are repeated as previously described. The results of 0-4 leaching stages are shown in FIG. 7.

Example 3

Preparation of a Thoroughly Leached Feedstock.

25 grams of lignocellulosic feedstock is milled to a particle size capable of passing through 20 mesh. Leaching of the lignocellulosic feedstock is performed by combining the lignocellulosic feedstock with 10 times the volume of its maximum water carrying capacity and the slurry is stirred at 25° C. for 24 hours. After the incubation period, the leachate is removed from the leached feedstock and the feedstock is rinsed with about 2L of a water and pressed to a solids content of about 50%. The pressed, leached feedstock is a thoroughly leached feedstock.

The total leachable buffering agents of the feedstock is determined by titrating the leachate plus rinse water to pH 3 with 0.1N: $H_2SO_4$. The volume of titrant used is expressed as kg $H_2SO_4$ per tonne of dry lignocellulosic feedstock. This is a measure of the total leachable buffering agents of the feedstock.

Example 4

Maximum Water Holding Capacity of Feedstock

A sample of about 25 grams of lignocellulosic feedstock with known dry weight and moisture content is mechanically disrupted into particles of about equal size and that pass through 20 mesh. The lignocellulosic feedstock is sifted into a container, allowing the feedstock to pack under the influence of gravity. Water is added gradually to a known mass of feedstock in a test tube until the point at which additional water added is free water. This point is estimated as the point wherein water forms a thin continuous layer over the lignocellulosic feedstock. The test tube is tipped to remove free water. The wet feedstock is then weighed to determine the amount of water and feedstock present. The mass of water in the particles at this point is the maximum water holding capacity of the lignocellulosic feedstock for that particular amount and type of feedstock. The maximum water holding capacity per mass of lignocellulosic feedstock may be measured by dividing the mass of water required to reach the point wherein the addition of further water results in free water over the lignocellulosic feedstock, by the mass of the lignocellulosic feedstock. Thus, leaching lignocellulosic feedstock using 10 times the maximum water holding capacity per kilogram of dry lignocellulosic feedstock means that the mass of aqueous solution is equal to 10 times the product of the mass of the dry lignocellulosic feedstock in kilograms and the maximum water holding capacity per kilogram of feedstock.

Example 5

Method of Producing Ethanol

A 0.28 gram dry sample of Wiley-milled oat hull lignocellulosic feedstock is leached for 10 minutes in 2 ml of tap water. The leachate is removed and the lignocellulosic feedstock is pressed to about 50% (w/v) solids content and subsequently, the leached feedstock is placed in 7 grams of 1% sulfuric acid (pH 0.6 to 0.9) in a sealed stainless steel "bomb" reactor. The capacity of the bomb reactor is 9 ml. The bomb reactor is placed in a preheated 290° C. oil bath for 50 seconds, and then cooled under tap water. The leached feedstock is now referred to as a pretreated feedstock Thermocouple measurements showed that the temperature in the interior of the bomb reached 260° C. by the end of the heating period. The average equivalent temperature was 235° C.

The pretreated feedstock is rinsed with tap water, and then vacuum-filtered over glass microfiber filter paper. The filter cakes are washed with tap water and air dried.

The pretreated feedstock is subjected to hydrolysis by cellulase as follows. A sample of the pretreated feedstock corresponding to 0.05 grams of cellulose is added to a 25 ml flask with 4.9 grams of 0.05 M sodium citrate buffer, pH 4.8. Iogen Cellulase (140 Filter paper units (FPU)/ml) and Novozym 188 beta-glucosidase (1440 BGU/ml) are added to the flask in an amount corresponding to 9 FPU/gram cellulose and 125 BGU/gram cellulose.

The flask is placed on an Orbit gyrotory shaker at 50° C. and shaken for 20 hours at 250 RPM. At the end of this period, the contents of the flask is filtered over glass microfiber filter paper. The filtrate, which contains glucose and other sugars is pH adjusted, inoculated with a precultured mid log phase (about 400 Klett units) *S. cerevisiae* cell culture and the mixture is fermented anerobically at 30° C. with shaking for 48 hours. After 48 hours of incubation, the mixture is centrifuged to separate yeast from the medium containing ethanol. The ethanol may be purified by distillation.

Using the methods described herein for biomass processing and ethanol production, yields of about 300-340 liter ethanol per metric ton dry biomass have been produced.

Example 5 teaches washing of pretreated feedstock prior to converting cellulose to glucose and fermenting glucose to ethanol. However, it is also contemplated that the entire composition treated in the bomb reactor may be pH adjusted, treated with cellulase to convert cellulose to glucose and fermented to ethanol. In such an embodiment, xylose is not removed from the pretreated feedstock by washing. In still another embodiment, xylose may be removed from the pretreated feedstock and fermented independently of glucose produced from cellulose hydrolysis of the pretreated feedstock.

As will be evident to someone of skill in the art, fermentation of sugars such as, but not limited to glucose and xylose may be performed using a variety of microorganisms, such as, but not limited to yeast, bacteria or a combination thereof. Further, the organisms maybe genetically modified organisms. Also, as is evident to someone of skill in the art, there exists other fermentation conditions which may be employed in the method of the present invention.

Also, as is evident to someone of skill in the art, ethanol may be recovered and purified from cultures medium by an method know in the art. These processes are fully contemplated in embodiments of the method of the invention.

All References are herein Incorporated by Reference.

The present invention has been described with regard to preferred embodiments. However, it will be obvious to persons skilled in the art that a number of variations and modifications can be made without departing from the scope of the invention as described herein.

The embodiments of the invention in which an exclusive property or privilege is claimed are defined as follows:

1. A method of producing xylose comprising, in this order:
    a) leaching a lignocellulosic feedstock comprising greater than about 20% (w/w) cellulose, said leaching comprising contacting said feedstock with at least one aqueous solution of about pH 6 to about pH 9 for between about 2 minutes and about 5 hours, at a temperature of about 25° C. to about 80° C. to produce a leached feedstock and a leachate;
    b) removing leachate from said leached feedstock; and
    c) treating said leached feedstock with an aqueous solution at a temperature of at least about 100° C. and at a pH of about 0.5 to about 2.5 to produce a composition comprising xylose and a treated feedstock.

2. The method of claim 1, wherein said lignocellulosic feedstock is selected from the group consisting of sugar beet bagasse, soybean stover, corn stover, rice straw, rice hulls, barley straw, corn cobs, wheat straw, wheat chaff, oat hulls, corn fiber, wood fiber, switch grass, cord grass, rye grass, miscanthus, and a combination thereof.

3. The method of claim 2, wherein said lignocellulosic feedstock comprises mechanically disrupted feedstock.

4. The method of claim 3, wherein said mechanically disrupted feedstock is capable of passing through about 20 mesh.

5. The method of claim 2, wherein said lignocellulosic feedstock has an AX/NSP ratio of about 0.35 to about 0.45.

6. The method of claim 5, wherein said feedstock comprises wheat straw, wheat chaff, switch grass, corn stover, corn cobs, oat hulls, or a combination thereof.

7. The method of claim 3, wherein said disrupted feedstock is produced by shredding, milling, chopping, chipping, grinding or a combination thereof.

8. The method of claim 7, wherein said milling comprises Szego milling, Hammer milling, Wiley milling, or a combination thereof.

9. The method of claim 1, wherein said leaching is performed for a period between about 2 minutes and about 2 hours.

10. The method of claim 1, wherein the amount of aqueous solution of step (a) added during said leaching is between about 0.25 to about 10 times the maximum water holding capacity of said lignocellulosic feedstock, wherein the maximum water holding capacity is measured by:
    (i) mechanically disrupting a sample of the lignocellulosic feedstock;
    (ii) adding water to a known dry mass of the mechanically disrupted feedstock until the point at which additional water added is free water;
    (iii) determining the mass of water required to reach the point at which additional water added is free water; and
    (iv) dividing the mass of water determined in step (iii) by the known dry mass of mechanically disrupted feedstock to obtain a value representing the maximum water holding capacity.

11. The method of claim 10, wherein the amount of aqueous solution added during said leaching is about 1.5 to 3 times the maximum water holding capacity of said lignocellulosic feedstock.

12. The method of claim 1, wherein said at least one aqueous solution of step (a) comprises water, mill water, process water, a leachate or a combination thereof.

13. The method of claim 1, wherein said pH of the at least one aqueous solution of step (a) is adjusted using NaOH, $H_2SO_4$, or a combination thereof.

14. The method of claim 1, wherein said leaching comprises a plurality of leaching stages.

15. The method of claim 14, wherein said leaching stages comprise 2 to 4 leaching stages.

16. The method of claim 14, wherein said plurality of leaching stages are performed such that leachate removed from a downstream leaching stage is added to an upstream leaching stage.

17. The method of claim 1, wherein said leaching removes between about 50% to about 100% of the total leachable buffering agents from the lignocellulosic feedstock.

18. The method of claim 1, wherein said leaching removes between about 70% to about 100% of the total leachable buffering agents from the lignocellulosic feedstock.

19. The method of claim 18, wherein said leaching removes between about 90% to about 100% of the total leachable buffering agents from the lignocellulosic feedstock.

20. The method of claim 1, wherein the treating of step (c) is performed using an acid selected from the group consisting of sulfuric acid, nitric acid and hydrochloric acid.

21. The method of claim 20, wherein said acid is sulfuric acid.

22. The method of claim 1, wherein said leachate is sampled during leaching, following leaching or both, and wherein conditions of the leaching are adjusted accordingly.

23. The method of claim 1, wherein the xylose is a xylose monomer.

24. The method of claim 1, wherein said composition produced from said method comprises a xylose concentration in the range of about 150 mg to about 260 mg of xylose per gram of feedstock.

25. The method of claim 1, wherein said treated feedstock has increased accessibility to being digested with cellulase enzymes.

26. The method of claim 1, wherein said method further comprises cellulase treatment of said treated feedstock.

27. The method of claim 10, wherein said method further comprises cellulase treatment of said treated feedstock.

28. The method of claim 1, wherein said at least one aqueous solution of step (a) comprises less than about 10 g/l impurities.

29. The method of claim 1, wherein said lignocellulosic feedstock comprises cellulose in an amount greater than about 30% (w/w).

30. The method of claim 1, wherein said lignocellulosic feedstock comprises a lignin content in an amount greater than about 5% (w/w).

31. The method of claim 1, wherein said lignocellulosic feedstock comprises a combined sugar content of sucrose, fructose and starch of less than about 20% (w/w).

32. The method of claim 1, wherein said lignocellulosic feedstock comprises oat hulls, wheat straw, switch grass, or a combination thereof.

33. The method of producing xylose according to claim 3, wherein said contacting with said at least one aqueous solution is for a period of about 2 minutes to about 2 hours using a volume of the at least one aqueous solution which is between about 0.25 and about 10 times the maximum water holding capacity of said disrupted lignocellulosic feedstock per kilogram of dried feedstock.

34. The method of claim 1, further comprising, prior to said leaching step (a), heating said lignocellulosic feedstock to about 80° C.

35. The method of claim 1, wherein in said leaching step (a), the lignocellulosic feedstock is incubated within a leaching bath and debris is removed.

36. The method of claim 35, wherein in said leaching step (a), said lignocellulosic feedstock is incubated from about 5 to about 30 minutes.

37. The method of claim 1, wherein said step (b) of removing said leachate from said leached feedstock comprises crushing said leached feedstock to produce a pressate and a solid feedstock, said pressate comprising soluble protein which is further processed for animal feed.

38. A method of producing ethanol comprising, in this order:
   a) preparing said composition comprising xylose and treated feedstock according to claim 1;
   b) treating said composition comprising xylose and treated feedstock with cellulase under conditions which hydrolyse cellulose in said treated feedstock to glucose, producing a sugar solution comprising xylose and glucose; and
   c) fermenting said sugar solution to ethanol.

39. A method of producing ethanol, comprising:
   a) preparing said composition comprising xylose and treated feedstock according to claim 1; and
   b) treating said composition with a microorganism under conditions which permit fermentation of said xylose in said composition to ethanol.

40. A method of producing ethanol comprising, in this order:
   a) preparing said composition comprising xylose and treated feedstock according to claim 1;
   b) separating said treated feedstock from said composition;
   c) treating said treated feedstock with cellulase under conditions that hydrolyze cellulose in said treated feedstock to glucose, producing a sugar solution comprising glucose; and
   d) fermenting said sugar solution to ethanol.

41. The method of claim 1, wherein leaching is performed at a temperature of about 60° C. to about 80° C.

42. The method of claim 41, wherein said at least one aqueous solution of step (a) comprises about 0.25 to about 10 times the maximum water holding capacity per kilogram of dry lingocellulosic feedstock.

43. The method of claim 1, wherein leaching is performed for a period between about 10 minutes and about 30 minutes.

44. The method of claim 42, wherein leaching is performed at a temperature of about 70° C.

45. The method of claim 42, wherein the aqueous solution has a pH of about 6 to about 7.

46. The method of claim 42, wherein said leached feedstock is treated in step (c) at a temperature of about 100° C. to about 220° C.

47. The method of claim 46, wherein said leached feedstock is treated for about 5 seconds to about 60 minutes.

48. The method of claim 1, wherein said treatment of step (c) comprises a first stage at a temperature between about 100° C. to about 180° C. followed by a second stage at a temperature between about 180° C. to about 270° C.

49. The method of claim 48, wherein said first stage is performed between about 0.25 to about 24 hours.

50. The method of claim 49, wherein said second stage is performed between about 5 to about 120 seconds.

51. A method of producing xylose and glucose comprising, in this order:
   a) leaching a mechanically-disrupted or preconditioned lignocellulosic feedstock comprising greater than about 20% (w/w) cellulose, said leaching being conducted prior to any chemical treatment of said lignocellulosic feedstock, comprising contacting said feedstock with at least one aqueous solution of pH 6 to 9 for a period greater than 2 minutes at a temperature of 25° C. to about 80° C. to produce a leached feedstock and a leachate;

b) removing the leachate from said leached feedstock; and c) treating said leached feedstock with an aqueous solution at a temperature of at least about 100° C. with ammonia under conditions which disrupt fiber structure of the leached feedstock and hydrolyze a portion of hemicellulose in said leached feedstock to produce a composition comprising a treated feedstock; and d) treating said composition with an enzyme comprising cellulase under conditions which hydrolyze cellulose in said leached feedstock to glucose, thereby producing a sugar solution comprising xylose and glucose.

52. The method of claim 1, wherein during step (b), between about 20 % and about 100% of the leachate is removed from the leached feedstock.

53. The method of claim 51, wherein said leaching is conducted for a period of between about 10 minutes and about 5 hours.

* * * * *

UNITED STATES PATENT AND TRADEMARK OFFICE
CERTIFICATE OF CORRECTION

PATENT NO. : 7,901,511 B2
APPLICATION NO. : 10/467741
DATED : March 8, 2011
INVENTOR(S) : Robert Griffin et al.

It is certified that error appears in the above-identified patent and that said Letters Patent is hereby corrected as shown below:

COLUMN 2

Line 59, "chiped" should read --chipped--.

COLUMN 3

Line 13, "of the" (second occurrence) should be deleted;
Line 24, "vapour" should read --vapor--;
Line 26, "vapour" should read --vapor--; and
Line 55, "line" should read --lined--.

COLUMN 4

Line 26, "comprises" should read --comprises:--.

COLUMN 5

Line 13, "Teachings," should read --leachings,--; and
Line 62, "comprising," should read --comprising:--.

COLUMN 6

Line 16, "comprising," should read --comprising:--; and
Line 38, "comprising," should read --comprising:--.

COLUMN 7

Line 47, "liter" should read --liters--.

Signed and Sealed this
Seventeenth Day of May, 2011

David J. Kappos
*Director of the United States Patent and Trademark Office*

COLUMN 10

Line 38, "is" should read --are--; and
Line 56, "agents'" should read --agents--.

COLUMN 11

Line 64, "vapour" should read --vapor--.

COLUMN 12

Line 34, "biomass hydrolysis" should read --biomass hydrolysis as disclosed in--; and
Line 65, "sutaible" should read --suitable--.

COLUMN 13

Line 67, "steam" should read --Steam--.

COLUMN 16

Line 36, "to" (second occurrence) should be deleted;
Line 46, "teachings" should read --leachings--;
Line 52, "teachings" should read --leachings--;
Line 56, "teachings" should read --leachings--; and
Line 60, "teachings" should read --leachings--.

COLUMN 17

Line 14, "maybe" should read --may be--;
Line 16, "teachings" should read --leachings--;
Line 37, "teachings" should read --leachings--;
Line 38, "feedstock" should read --feedstock.--;
Line 39, "teachings" should read --leachings--; and
Line 46, "Teachings" should read --leachings--.

COLUMN 26

Line 37, "lingocellulosic" should read --lignocellulosic--.